(12) United States Patent (10) Patent No.: US 7,511,084 B2
Noe et al. (45) Date of Patent: Mar. 31, 2009

(54) ACYL- AND BISACYLPHOSPHINE DERIVATIVES

(75) Inventors: Ralf Noe, Mannheim (DE); Andreas Henne, Neustadt (DE); Matthias Maase, Speyer (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 778 days.

(21) Appl. No.: 10/502,658

(22) PCT Filed: Feb. 4, 2003

(86) PCT No.: PCT/EP03/01053

§ 371 (c)(1), (2), (4) Date: Aug. 4, 2004

(87) PCT Pub. No.: WO03/068784

PCT Pub. Date: Aug. 21, 2003

(65) Prior Publication Data

US 2005/0222294 A1 Oct. 6, 2005

(30) Foreign Application Priority Data

Feb. 13, 2002 (DE) .............................. 102 06 117

(51) Int. Cl.
*C08F 2/46* (2006.01)
(52) U.S. Cl. .............................. 522/64; 522/28; 522/30; 522/7
(58) Field of Classification Search ...................... 522/7, 522/64, 28, 30
See application file for complete search history.

(56) References Cited

U.S. PATENT DOCUMENTS

| 5,472,992 | A | 12/1995 | Leppard et al. | |
|---|---|---|---|---|
| 5,683,615 | A | 11/1997 | Munoz | |
| 6,207,727 | B1 * | 3/2001 | Beck et al. | 522/64 |

FOREIGN PATENT DOCUMENTS

| DE | 196 50 562 | 6/1998 |
|---|---|---|
| EP | 007 508 | 2/1980 |
| EP | 062 839 | 10/1982 |
| EP | 487 453 | 5/1992 |
| EP | 600 373 | 6/1994 |
| EP | 615 980 | 9/1994 |
| EP | 724 194 | 7/1996 |
| JP | 01-62927 | 3/1989 |
| JP | 3-010241 | 1/1991 |
| JP | 9-152689 | 6/1997 |
| WO | 00/32612 | 6/2000 |

OTHER PUBLICATIONS

Kolodiazhnyi et al., Simple route to chiral organo-phosphorus compounds, Tetrahedron: Asymmetry (1996), 7(4), 967-970. See Abstract.*

Kolodiazhnyi et al., Simple route to chiral organo-phosphorus compounds, Tetrahedron: Asymmetry (1996), 7(4), 967-970.*

Database Chemabs [Online] Chemical Abstracts Service, Columbus, Ohio, US Sal'keeva, L. K. et al: "Reactions of esters, thio esters and amides of phosphorus (III) acids wit acyl halides", retrieved from STN Database accession No. 118:39028 XP002236998 abstract & Zhurnal Obshchei Khimi (1992), 62 (2), 333-8.

Database Chemabs [Online] Chemical Abstracts Service, Columbus, Ohio, US Veits, Yu, A. et al: "Reaction of secondary phosphines with carbon tetrachloride. Synthesis of acylalkylchlorophosphines", retrieved from STN Database accession No. 115:92392 XP002236999 abstract & Zhurnal Obshchei Khimii (1991), 61(1), 130-5.

Database Chemabs [Online] Chemical Abstracts Service, Columbus Ohio, US Veits, Yu. A. et al: "tert-Butylpivaloylphosphonous acid and its derivatives" retrieved from STN Database accession No. 115:71748 XP002237000 abstract & Zhurnal Obshchei Khimii (1991), 61(1) 124-30.

Database Chemabs [Online] Chemical Abstracts Service, Columbus, Ohio, US Veits, Yu. A. et al: "Synthesis and properties of acyltrialkyldiphosphines", retrieved from STN Database accession No. 114:62212 XP002237001 abstract & Zhurnal Obshchei Khimii (1990), 60(9), 2028-36.

Database Chemabs [Online] Chemical Abstracts Service, Columbus, Ohio, US Gazizov, T.K. et al: "Reaction of diethyls-butyl thiophosphite with acyl chlorides" retrieved from STN Database accession No. 112:179121 XP002237002 abstract & Zhurnal Obshchei Khimii (1989), 59(8), 1913-15.

Database Chembas [Online] Chemical Abstracts Service, Columbus, Ohio, US Sinyashin, O.G. et al: "Reaction of tert-butyl(ethylthio)phosphine with carboxylic acid chlorides", retrieved from STN Database accession No. 111:78181 XP002237003 abstract & Zhurnal Obshchei Khimii (1988), 58(10), 2206-12.

(Continued)

*Primary Examiner*—Daniel M Sullivan
*Assistant Examiner*—Chukwuma O Nwaonicha
(74) *Attorney, Agent, or Firm*—Oblon, Spivak, McClelland, Maier & Neustadt, P.C.

(57) ABSTRACT

The invention relates to the acyl- and bisacylphosphine derivatives according to formula (I), wherein Y represents O, S, $NR^3$, $N-OR^3$ or $N-NR^3R^4$, Z represents O, S, $NR^3$, $N-OR^3$, $N-NR^3R^4$ or a free pair of electrons, and FG represents a leaving group and the remaining groups are defined as in the description. The invention further relates to a method for the production of the inventive derivatives and to their use.

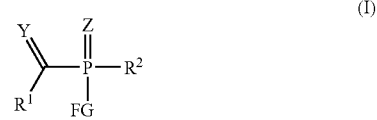

(I)

19 Claims, No Drawings

OTHER PUBLICATIONS

Database Chemabs [Online] Chemical Abstracts Service, Columbus, Ohio, US Kim, T.V. et al: "Vinyl esters of phosphorus acids. XVI. Chemical properties of alkyl(alken-1-yl) chlorophosphites" retrieved from STN Database accession No. 90:38497 XP002237004 abstract & Zhurnal Obshcei Khimii (1978), 48(9), 1967-76.

Database Chemabs [Online] Chemical Abstracts Service, Columbus, Ohio, US Novitskii, K.I. et al: Reaction of. Beta.,.gamma.-unsaturated acid chlorides with cyclic glycol chlorophosphites retrieved from STN Database accession No. 67:32743 XP002237005 abstract & Zhurnal Obshchei Khimii (1967), 37(2), 512.

E. Andrew Boyd, et al., "Facile synthesis of functionalised phenylphosphinic acid derivatives", Tetrahedron Letters, vol. 37, No. 10 pp. 1651-1654, 1996.

* cited by examiner

ACYL- AND BISACYLPHOSPHINE DERIVATIVES

The present invention relates to reactive acyl- and bisacylphosphine derivatives, to a process for their preparation, and to their use.

Acyl- and bisacylphosphine oxides and the use thereof as photoinitiators have been known for some time.

JP 10-62927, JP 9-152689, EP-A 724 194 and JP 3-10241 disclose compounds having a phosphine oxide structure which carry a hydroxylamino or alkoxylamino group or a hydrazido group on the central phosphorus atom and which are used in photographic materials.

U.S. Pat. No. 5,683,615 discloses magnetorheological liquids which comprise dialkyl dithiophosphates.

Also known are derivatives of acylphosphine oxides, for example those which carry an unsubstituted or substituted amino group, a hydroxyl group or an —O-M$^+$ group, where M$^+$ is an equivalent of a cation, on the central phosphorus atom (EP-A 62 839), a $C_1$-$C_{12}$-alkoxy group (DE-A 196 50 562), an aryloxy group (EP-A 600 373) or a silyloxy group (EP-A 487 453), and which can likewise be used as photoinitiators.

Many of the photoinitiators used hitherto have the problem that residues or degradation products of photoinitiators are able to diffuse out of the cured coating into the surrounding medium (migration), where they can cause problems, for example if the medium is a packaging material for foods.

Furthermore, the low solubility and incorporation ability of certain phosphine oxides are limited, which means that there continues to be a demand for other phosphine oxides having improved interactions for radiation-curable surface-coating systems.

There continues to be a demand in free-radical polymerization for highly reactive photoinitiator systems which are easy to prepare and easy to handle. Furthermore, such systems should be thermally stable and stable on storage.

EP-B 7 508 discloses the synthesis of acylphosphine oxides in an Arbusov rearrangement by reaction of alkoxyphosphines and acid chlorides:

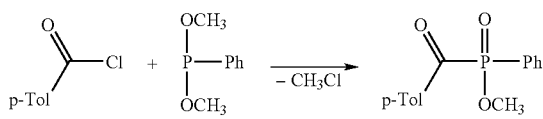

where p-Tol=4-methylphenyl, and Ph=phenyl.

U.S. Pat. No. 5,472,992 discloses the synthesis of bisacylphosphines in which a phosphine is diacylated in the presence of a base and subsequently oxidized.

However, these synthetic methods have the disadvantage that volatile, toxic and foul-smelling phosphines have to be used.

WO 00/32612 furthermore discloses the synthesis of acyl- and bisacylphosphines in which an organic phosphoryl halide is brought into contact with an alkali metal or magnesium/lithium, and the resultant metallated phosphines are then reacted with an acid chloride:

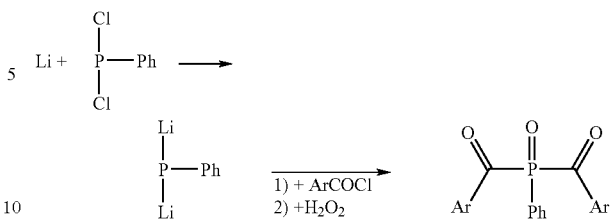

where Ph=phenyl and Ar=aryl.

However, a reaction of this type requires complex handling of, for example, metallic lithium for the metallation.

A common feature of these syntheses is that they are restricted by their substrates, and the products can thus only be varied in narrow limits.

It is an object of the present invention to provide compounds which enable the simple synthesis of novel acyl- and bisacylphosphine derivatives having a high tolerance to functional groups and which can themselves likewise be employed as photoinitiators with a very low tendency to migrate.

We have found that this object is achieved by acyl- or bisacylphosphine derivatives of the formula (I)

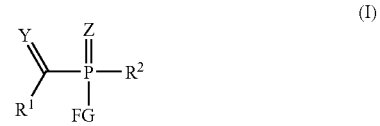

where
$R^1$, $R^2$, $R^5$, $R^6$ and $R^7$ are $C_1$-$C_{18}$-alkyl, or $C_2$-$C_{18}$-alkyl, $C_2$-$C_{18}$-alkenyl, $C_6$-$C_{12}$-aryl or $C_5$-$C_{12}$-cycloalkyl, each of which is uninterrupted or interrupted by one or more oxygen and/or sulfur atoms and/or one or more substituted or unsubstituted imino groups, or are a five- to six-membered heterocyclic radical containing oxygen, nitrogen and/or sulfur atoms, where the said radicals may each be substituted by aryl, alkyl, aryloxy, alkoxy, heteroatoms and/or heterocyclic radicals,
$R^2$ is furthermore $C_1$-$C_{18}$-alkoxy, which is unsubstituted or substituted by aryl, alkyl, aryloxy, alkoxy, heteroatoms and/or heterocyclic radicals, or is $R^1$—(C=Y)—,
Y is O, S, NR$^3$, N—OR$^3$ or N—NR$^3$R$^4$,
Z is O, S, NR$^3$, N—OR$^3$, N—NR$^3$R$^4$ or a free pair of electrons,
$R^3$ is hydrogen, $C_1$- to $C_4$-alkyl, —SO$_3$H, phenyl or acetyl,
$R^4$ is hydrogen, $C_1$- to $C_4$-alkyl, COOR$^3$, arylsulfonyl, or $C_6$-$C_{12}$-aryl which is unsubstituted or substituted by aryl, alkyl, aryloxy, alkoxy, heteroatoms and/or heterocyclic radicals,
FG is a leaving group having the structure —F, —Cl, —I, —CN, —OCN, —SCN, —N$^+$R$^6$R$^7$R$^8$, —O(CO)R$^5$, —O(CO)OR$^5$, —O(SO)Cl, —O(SO$_2$)Cl, —O(SO$_2$)R$^5$, —O(CO)Cl, —O(NO)OR$^5$ or, in the case where Z≠S, —SR$^5$,
$R^5$ is furthermore $C_1$-$C_{18}$-alkoxy, which is unsubstituted or substituted by aryl, alkyl, aryloxy, alkoxy, heteroatoms and/or heterocyclic radicals, and
$R^8$ is $C_1$-$C_{18}$-alkyl, which is unsubstituted or substituted by aryl, alkyl, aryloxy, alkoxy, heteroatoms and/or heterocyclic radicals, or $C_2$-$C_{18}$-alkyl, which is uninterrupted or interrupted by one or more oxygen and/or sulfur atoms and/or one or more substituted or unsubstituted imino groups.

In these formulae, $C_1$-$C_{18}$-alkyl which is unsubstituted or substituted by aryl, alkyl, aryloxy, alkoxy, heteroatoms and/or heterocyclic radicals is, for example, methyl, ethyl, propyl, isopropyl, n-butyl, sec-butyl, tert-butyl, pentyl, hexyl, heptyl, octyl, 2-ethylhexyl, 2,4,4-trimethylpentyl, decyl, dodecyl, tetradecyl, heptadecyl, octadecyl, 1,1-dimethylpropyl, 1,1-dimethylbutyl, 1,1,3,3-tetramethylbutyl, benzyl, 1-phenylethyl, 2-phenylethyl, α,α-dimethylbenzyl, benzhydryl, p-tolylmethyl, 1-(p-butylphenyl)ethyl, p-chlorobenzyl, 2,4-dichlorobenzyl, p-methoxybenzyl, m-ethoxybenzyl, 2-cyanoethyl, 2-cyanopropyl, 2-methoxycarbonylethyl, 2-ethoxycarbonylethyl, 2-butoxycarbonylpropyl, 1,2-di(methoxycarbonyl)ethyl, 2-methoxyethyl, 2-ethoxyethyl, 2-butoxyethyl, diethoxymethyl, diethoxyethyl, 1,3-dioxolan-2-yl, 1,3-dioxan-2-yl, 2-methyl-1,3-dioxolan-2-yl, 4-methyl-1,3-dioxolan-2-yl, 2-isopropoxyethyl, 2-butoxypropyl, 2-octyloxyethyl, chloromethyl, 2-chloroethyl, trichloromethyl, trifluoromethyl, 1,1-dimethyl-2-chloroethyl, 2-methoxyisopropyl, 2-ethoxyethyl, butylthiomethyl, 2-dodecylthioethyl, 2-phenylthioethyl, 2,2,2-trifluoroethyl, 2-hydroxyethyl, 2-hydroxypropyl, 3-hydroxypropyl, 4-hydroxybutyl, 6-hydroxyhexyl, 2-aminoethyl, 2-aminopropyl, 3-aminopropyl, 4-aminobutyl, 6-aminohexyl, 2-methylaminoethyl, 2-methylaminopropyl, 3-methylaminopropyl, 4-methylaminobutyl, 6-methylaminohexyl, 2-dimethylaminoethyl, 2-dimethylaminopropyl, 3-dimethylaminopropyl, 4-dimethylaminobutyl, 6-dimethylaminohexyl, 2-hydroxy-2,2-dimethylethyl, 2-phenoxyethyl, 2-phenoxypropyl, 3-phenoxypropyl, 4-phenoxybutyl, 6-phenoxyhexyl, 2-methoxyethyl, 2-methoxypropyl, 3-methoxypropyl, 4-methoxybutyl, 6-methoxyhexyl, 2-ethoxyethyl, 2-ethoxypropyl, 3-ethoxypropyl, 4-ethoxybutyl or 6-ethoxyhexyl, $C_1$-$C_{18}$-alkoxy which is unsubstituted or substituted by aryl, alkyl, aryloxy, alkoxy, heteroatoms and/or heterocyclic radicals is, for example, methoxy, ethoxy, n-propoxy, isopropoxy, n-butoxy, iso-butoxy, sec-butoxy, tert-butoxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 8-methoxy-1,5-dioxooctyl, 12-methoxy-1,5,9-trioxooctyl, 16-methoxy-1,5,9,13-tetraoxohexadecyl, 8-ethoxy-1,5-dioxooctyl, 12-ethoxy-1,5,9-trioxooctyl, 16-ethoxy-1,5,9,13-tetraoxohexadecyl, 10-hydroxy-1,6-dioxodecyl, 15-hydroxy-1,6,11-trioxopentadecyl, 10-methoxy-1,6-dioxodecyl, 15-methoxy-1,6,11-trioxopentadecyl, 10-ethoxy-1,6-dioxodecyl or 15-ethoxy-1,6,11-trioxopentadecyl, $C_2$-$C_{18}$-alkyl which is uninterrupted or interrupted by one or more oxygen and/or sulfur atoms and/or one or more substituted or unsubstituted imino groups is, for example, 5-hydroxy-3-oxapentyl, 8-hydroxy-3,6-dioxaoctyl, 11-hydroxy-3,6,9-trioxaundecyl, 7-hydroxy-4-oxaheptyl, 11-hydroxy-4,8-dioxaundecyl, 15-hydroxy-4,8,12-trioxapentadecyl, 9-hydroxy-5-oxanonyl, 14-hydroxy-5,10-oxatetradecyl, 5-methoxy-3-oxapentyl, 8-methoxy-3,6-dioxaoctyl, 11-methoxy-3,6,9-trioxaundecyl, 7-methoxy-4-oxaheptyl, 11-methoxy-4,8-dioxaundecyl, 15-methoxy-4,8,12-trioxapentadecyl, 9-methoxy-5-oxanonyl, 14-methoxy-5,10-oxatetradecyl, 5-ethoxy-3-oxapentyl, 8-ethoxy-3,6-dioxaoctyl, 11-ethoxy-3,6,9-trioxaundecyl, 7-ethoxy-4-oxaheptyl, 11-ethoxy-4,8-dioxaundecyl, 15-ethoxy-4,8,12-trioxapentadecyl, 9-ethoxy-5-oxanonyl or 14-ethoxy-5,10-oxatetradecyl.

The number of oxygen atoms and/or sulfur atoms and/or imino groups is unrestricted. In general, it is not more than 5 in the radical, preferably not more than 4 and very particularly preferably not more than 3.

Furthermore, at least one carbon atom, preferably at least two carbon atoms, are located between two heteroatoms.

Substituted and unsubstituted imino groups can be, for example, imino, methylimino, iso-propylimino, n-butylimino or tert-butylimino.

Furthermore, $C_2$-$C_{18}$-alkenyl which is unsubstituted or substituted by aryl, alkyl, aryloxy, alkoxy, heteroatoms and/or heterocyclic radicals is, for example, vinyl, 1-propenyl, allyl, methallyl, 1,1-dimethylallyl, 2-butenyl, 2-hexenyl, octenyl, undecenyl, dodecenyl, octadecenyl, 2-phenylvinyl, 2-methoxyvinyl, 2-ethoxyvinyl, 2-methoxyallyl, 3-methoxyallyl, 2-ethoxyallyl, 3-ethoxyallyl or 1- or 2-chlorovinyl, $C_6$-$C_{12}$-aryl which is unsubstituted or substituted by aryl, alkyl, aryloxy, alkoxy, heteroatoms and/or heterocyclic radicals is, for example, phenyl, tolyl, xylyl, α-naphthyl, β-naphthyl, 4-biphenylyl, chlorophenyl, dichlorophenyl, trichlorophenyl, difluorophenyl, methylphenyl, dimethylphenyl, trimethylphenyl, ethylphenyl, diethylphenyl, iso-propylphenyl, tert-butylphenyl, dodecylphenyl, methoxyphenyl, dimethoxyphenyl, ethoxyphenyl, hexyloxyphenyl, methylnaphthyl, isopropylnaphthyl, chloronaphthyl, ethoxynaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, methoxyethylphenyl or ethoxymethylphenyl, $C_5$-$C_{12}$-cycloalkyl which is unsubstituted or substituted by aryl, alkyl, aryloxy, alkoxy, heteroatoms and/or heterocyclic radicals is, for example, cyclopentyl, cyclohexyl, cyclooctyl, cyclododecyl, methylcyclopentyl, dimethylcyclopentyl, methylcyclohexyl, dimethylcyclohexyl, diethylcyclohexyl, butylcyclohexyl, methoxycyclohexyl, dimethoxycyclohexyl, diethoxycyclohexyl, butylthiocyclohexyl, chlorocyclohexyl, dichlorocyclohexyl, dichlorocyclopentyl and a saturated or unsaturated bicyclic system, for example norbornyl or norbornenyl, a five- to six-membered, oxygen, nitrogen and/or sulfur atom-containing heterocyclic radical is, for example, furyl, thiophenyl, pyrryl, pyridyl, indolyl, benzoxazolyl, dioxolyl, dioxyl, benzimidazolyl, benzothiazolyl, dimethylpyridyl, methylquinolyl, dimethylpyrryl, methoxyfuryl, dimethoxypyridyl, difluoropyridyl, methylthiophenyl, isopropylthiophenyl or tert-butylthiophenyl, $C_1$ to $C_4$-alkyl is, for example, methyl, ethyl, propyl, isopropyl, n-butyl, sec-butyl or tert-butyl, and $C_6$-$C_{12}$-aryl or arylsulfonyl, each which is unsubstituted or substituted by aryl, alkyl, aryloxy, alkoxy, heteroatoms and/or heterocyclic radicals, is, for example, phenyl, 2,6-dinitrophenyl, 2,4-dinitrophenyl, 2-nitrophenyl, 4-nitrophenyl, formyl, acetyl, propionyl, carbamoyl, phenylsulfonyl or 4-methylphenylsulfonyl.

The number of substituents in the stated radicals is unrestricted. In general, it is up to 3 substituents, preferably up to 2 substituents and particularly preferably up to one substituent, in radicals having from one to three carbon atoms. In radicals having from four to six carbon atoms, it is generally up to 4 substituents, preferably up to 3 substituents and particularly preferably up to one substituent. In radicals having more than seven carbon atoms, it is generally up to 6 substituents, preferably up to 4 substituents and particularly preferably up to two substituents.

$R^1$ is preferably phenyl, tolyl, xylyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or ortho-substituted phenyls, such as 2-methylphenyl, 2-methoxyphenyl or 2-chlorophenyl.

$R^1$ is particularly preferably phenyl, tolyl, α-naphthyl, β-naphthyl, 2,6- or 2,4-dichlorophenyl, 2,4,6-trichlorophenyl, 2,6- or 2,4-dimethylphenyl, 2,4,6-trimethylphenyl, 2,6- or 2,4-diethylphenyl, 2-iso-propylphenyl, 2-tert-butylphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 2,6-dinitrophenyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2-methylphenyl, 2-methoxyphenyl or 2-chlorophenyl.

$R^1$ is very particularly preferably phenyl, α-naphthyl, 2,6-dichlorophenyl, 2,4,6-trichlorophenyl, 2,6-dimethylphenyl, 2,4,6-trimethylphenyl, 2,6-diethylphenyl, 2,6-dimethoxyphenyl, 2,6-diethoxyphenyl, 2,6-dimethylphenyl, 2,4,6-trimethylphenyl, 2,6-dimethoxyphenyl, 2,6-dichlorophenyl, 2,6-dinitrophenyl, 2,6-dimethylcyclohexyl, 2,6-diethylcyclohexyl, 2,6-dimethoxycyclohexyl, 2,6-diethoxycyclohexyl or 2,6-dichlorocyclohexyl.

$R^1$ is in particular phenyl, 2,6-dichlorophenyl, 2,4,6-trichlorophenyl, 2,6-dimethylphenyl, 2,4,6-trimethylphenyl or 2,6-dimethoxyphenyl.

$R^2$ is preferably 2,4,4-trimethylpentyl, benzyl, p-chlorobenzyl, 2,4-dichlorobenzyl, p-methoxybenzyl, methoxy, ethoxy, n-propoxy, iso-propoxy, n-butoxy, iso-butoxy, sec-butoxy, tert-butoxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, vinyl, 1-propenyl, allyl, methallyl, 1,1-dimethylallyl, 2-butenyl, 2-hexenyl, 2-phenylvinyl, 2-methoxyvinyl, 2-ethoxyvinyl, 2-chlorovinyl, phenyl, tolyl, xylyl, α-naphthyl, β-naphthyl, 4-biphenylyl, 2-, 3- or 4-chlorophenyl, 2,4- or 2,6-dichlorophenyl, 2,4,6-trichlorophenyl, 2-, 3- or 4-methylphenyl, 2,4- or 2,6-dimethylphenyl, 2,4,6-trimethylphenyl, 2-, 3- or 4-ethylphenyl, 2,4- or 2,6-diethylphenyl, 2-, 3- or 4-iso-propylphenyl, 2-, 3- or 4-tert-butylphenyl, 2-, 3- or 4-methoxyphenyl, 2,4- or 2,6-dimethoxyphenyl, 2-, 3- or 4-ethoxyphenyl, methylnaphthyl, chloronaphthyl, ethoxynaphthyl, 2,6-dimethylphenyl, 2,4,6-trimethylphenyl, 2,4- or 2,6-dimethoxyphenyl, 2,4- or 2,6-dichlorophenyl, 2- or 4-nitrophenyl, 2,4- or 2,6-dinitrophenyl, 4-dimethylaminophenyl, 4-acetylphenyl or $R^1$—(C=Y)—.

$R^2$ is particularly preferably benzyl, p-chlorobenzyl, 2,4-dichlorobenzyl, p-methoxybenzyl, methoxy, ethoxy, n-propoxy, iso-propoxy, n-butoxy, iso-butoxy, sec-butoxy, tert-butoxy, 6-hydroxy-1,4-dioxohexyl, 9-hydroxy-1,4,7-trioxononyl, 12-hydroxy-1,4,7,10-tetraoxododecyl, 6-methoxy-1,4-dioxohexyl, 9-methoxy-1,4,7-trioxononyl, 12-methoxy-1,4,7,10-tetraoxododecyl, 6-ethoxy-1,4-dioxohexyl, 9-ethoxy-1,4,7-trioxononyl, 12-ethoxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, vinyl, 2-butenyl, 2-phenylvinyl, phenyl, tolyl, xylyl, α-naphthyl, β-naphthyl, 4-biphenylyl, 2-, 3- or 4-chlorophenyl, 2,4- or 2,6-dichlorophenyl, 2,4,6-trichlorophenyl, 2-, 3- or 4-methylphenyl, 2,4- or 2,6-dimethylphenyl, 2,4,6-trimethylphenyl, 2-, 3- or 4-ethylphenyl, 2-, 3- or 4-iso-propylphenyl, 2-, 3- or 4-tert-butylphenyl, 2-, 3- or 4-methoxyphenyl, 2,4- or 2,6-dimethoxyphenyl, 2-, 3- or 4-ethoxyphenyl, methylnaphthyl, chloronaphthyl, ethoxynaphthyl, 2- or 4-nitrophenyl, 2,4- or 2,6-dinitrophenyl, 4-dimethylaminophenyl, 4-acetylphenyl or $R^1$—(C=Y)—.

$R^2$ is very particularly preferably methoxy, ethoxy, n-propoxy, iso-propoxy, n-butoxy, sec-butoxy, iso-butoxy, tert-butoxy, 6-hydroxy-1,4-dioxohexyl, 9-hydroxy-1,4,7-trioxononyl, 12-hydroxy-1,4,7,10-tetraoxododecyl, 8-hydroxy-1,5-dioxooctyl, 12-hydroxy-1,5,9-trioxooctyl, 16-hydroxy-1,5,9,13-tetraoxohexadecyl, 10-hydroxy-1,6-dioxodecyl, 15-hydroxy-1,6,11-trioxopentadecyl, phenyl, xylyl, α-naphthyl, β-naphthyl, 4-biphenylyl, 2-, 3- or 4-chlorophenyl, 2,4-dichlorophenyl, 2-, 3- or 4-methylphenyl, 2,4-dimethylphenyl, 2-, 3- or 4-ethylphenyl, 2-, 3- or 4-methoxyphenyl, 2,4-dimethoxyphenyl, 2-, 3- or 4-ethoxyphenyl, methylnaphthyl, chloronaphthyl, ethoxynaphthyl, 2- or 4-nitrophenyl or $R^1$—(C=Y)—.

$R^2$ is in particular methoxy, ethoxy, n-propoxy, iso-propoxy, n-butoxy, sec-butoxy, iso-butoxy, tert-butoxy, phenyl, 4-biphenylyl, 2-, 3- or 4-chlorophenyl, 2-, 3- or 4-methylphenyl, 2-, 3- or 4-methoxyphenyl or 2-, 3- or 4-ethoxyphenyl. $R^2$ is especially phenyl, methoxy or ethoxy.

Y is preferably O, S or $NR^3$.

Y is particularly preferably O or S and very particularly preferably O.

Z is preferably O, S, $NR^3$ or a free pair of electrons, particularly preferably O, S or a free pair of electrons, very particularly preferably O or S and in particular O.

$R^3$ is preferably hydrogen, methyl, tert-butyl, phenyl or $SO_3H$, particularly preferably hydrogen, tert-butyl, phenyl or $SO_3H$ and very particularly preferably hydrogen, tert-butyl or phenyl.

$R^4$ is preferably hydrogen, methyl, phenyl, 2,4-dinitrophenyl, carbamoyl, phenylsulfonyl or 4-methylphenylsulfonyl, particularly preferably hydrogen, phenyl, 2,4-dinitrophenyl or phenylsulfonyl, very particularly preferably hydrogen, 2,4-dinitrophenyl or phenylsulfonyl and in particular hydrogen or 2,4-dinitrophenyl.

FG is preferably —Cl, —CN, —OCN, —SCN, —$N^+R^6R^7R^8$, —$O(CO)R^5$, —$O(CO)OR^5$, —(SO)Cl, —$(SO_2)R^5$, —$(SO_2)OR^5$ or —$O(CO)Cl$.

FG is particularly preferably —Cl, —CN, —OCN, —SCN, —$N^+R^6R^7R^8$, —$O(CO)R^5$, —$O(CO)OR^5$ or —$(SO_2)R^5$.

FG is very particularly preferably —Cl, —$O(CO)R^5$, —$O(CO)OR^5$ or —$(SO_2)R^5$ and in particular —Cl or —$(SO_2)R^5$.

$R^5$ is preferably methoxy, ethoxy, n-propoxy, n-butoxy, methyl, ethyl, n-propyl, n-butyl, tert-butyl, phenyl, 4-methylphenyl, trifluoromethyl or 4-bromophenyl.

$R^5$ is particularly preferably methoxy, ethoxy, n-butoxy, methyl, ethyl, n-butyl, phenyl, 4-methylphenyl, trifluoromethyl or 4-bromophenyl.

$R^5$ is very particularly preferably n-butoxy, methyl, ethyl, n-butyl, phenyl or 4-methylphenyl and in particular methyl or 4-methylphenyl.

$R^6$, $R^7$ and $R^8$, independently of one another, are preferably methyl, ethyl, n-propyl, n-butyl, benzyl, 2-hydroxyethyl, 2-hydroxypropyl, 2-cyanoethyl, 2-methoxycarbonylethyl, 2-ethoxycarbonylethyl or 2-butoxycarbonylethyl.

$R^6$, $R^7$ and $R^8$, independently of one another, are particularly preferably methyl, benzyl, 2-hydroxyethyl, 2-cyanoethyl, 2-methoxycarbonylethyl, 2-ethoxycarbonylethyl or 2-butoxycarbonylethyl.

$R^6$, $R^7$ and $R^8$, independently of one another, are very particularly preferably methyl, benzyl, 2-hydroxyethyl or 2-butoxycarbonylethyl and in particular methyl, 2-hydroxyethyl or 2-butoxycarbonylethyl.

Of the compounds described by the formula (I), particular preference is given to the following species I-1 to I-372, in which the radicals in the formula (I) have the following meanings:

| I- | $R^1$ | $R^2$ | Y | Z | FG |
|---|---|---|---|---|---|
| 1 | TMP | Ph | O | O | Cl |
| 2 | TMP | Ph | O | O | I |
| 3 | TMP | Ph | O | O | OCN |
| 4 | TMP | Ph | O | O | SCN |
| 5 | TMP | Ph | O | O | CN |
| 6 | TMP | Ph | O | O | Acetoxy (—O(CO)CH$_3$) |
| 7 | TMP | Ph | O | O | Benzoyloxy (—O(CO)Ph) |
| 8 | TMP | Ph | O | O | Formyloxy (—O(CO)H) |
| 9 | TMP | Ph | O | O | Methoxycarbonyloxy (—O(CO)OCH$_3$) |
| 10 | TMP | Ph | O | O | Ethoxycarbonyloxy (—O(CO)OCH$_2$CH$_3$) |
| 11 | TMP | Ph | O | O | n-Butoxycarbonyloxy (—O(CO)OCH$_2$CH$_2$CH$_2$CH$_3$) |
| 12 | TMP | Ph | O | O | Chlorocarbonyloxy (—O(CO)Cl) |
| 13 | TMP | Ph | O | O | Chlorosulfinyloxy (—O(SO)Cl) |
| 14 | TMP | Ph | O | O | Methoxysulfinyloxy (—O(SO)OCH$_3$) |
| 15 | TMP | Ph | O | O | Ethoxysulfinyloxy (—O(SO)OCH$_2$CH$_3$) |
| 16 | TMP | Ph | O | O | n-Butoxysulfinyloxy (—O(SO)OCH$_2$CH$_2$CH$_2$CH$_3$) |
| 17 | TMP | Ph | O | O | Chlorosulfuryloxy (—O(SO$_2$)Cl) |
| 18 | TMP | Ph | O | O | Methoxysulfuryloxy (—O(SO$_2$)OCH$_3$) |
| 19 | TMP | Ph | O | O | Ethoxysulfuryloxy (—O(SO$_2$)OCH$_2$CH$_3$) |
| 20 | TMP | Ph | O | O | Methylsulfonyloxy (—O(SO$_2$)CH$_3$) |
| 21 | TMP | Ph | O | O | Trifluoromethylsulfonyloxy (—O(SO$_2$)CF$_3$) |
| 22 | TMP | Ph | O | O | Benzenesulfonyloxy (—O(SO$_2$)Ph) |
| 23 | TMP | Ph | O | O | p-Toluenesulfonyloxy (—O(SO$_2$)Ph-4-CH$_3$) |
| 24 | TMP | Ph | O | O | Dodecylbenzenesulfonyloxy |
| 25 | TMP | Ph | O | O | p-Bromobenzenesulfonyloxy (—O(SO$_2$)Ph-4-Br) |
| 26 | TMP | Ph | O | O | Diethyl(2-hydroxyethyl)ammonium |
| 27 | TMP | Ph | O | O | Benzyldiethylammonium |
| 28 | TMP | Ph | O | O | Tris(2-hydroxyethyl)ammonium |
| 29 | TMP | Ph | O | O | Dimethyl(2-hydroxyethyl)ammonium |
| 30 | TMP | Ph | O | O | Benzyldimethylammonium |
| 31 | TMP | Ph | O | O | Trimethylammonium |
| 32 | TMP | OEt | O | O | Cl |
| 33 | TMP | OEt | O | O | I |
| 34 | TMP | OEt | O | O | OCN |
| 35 | TMP | OEt | O | O | SCN |
| 36 | TMP | OEt | O | O | CN |
| 37 | TMP | OEt | O | O | Acetoxy (—O(CO)CH$_3$) |
| 38 | TMP | OEt | O | O | Benzoyloxy (—O(CO)Ph) |
| 39 | TMP | OEt | O | O | Formyloxy (—O(CO)H) |
| 40 | TMP | OEt | O | O | Methoxycarbonyloxy (—O(CO)OCH$_3$) |
| 41 | TMP | OEt | O | O | Ethoxycarbonyloxy (—O(CO)OCH$_2$CH$_3$) |
| 42 | TMP | OEt | O | O | n-Butoxycarbonyloxy (—O(CO)OCH$_2$CH$_2$CH$_2$CH$_3$) |
| 43 | TMP | OEt | O | O | Chlorocarbonyloxy (—O(CO)Cl) |
| 44 | TMP | OEt | O | O | Chlorosulfinyloxy (—O(SO)Cl) |
| 45 | TMP | OEt | O | O | Methoxysulfinyloxy (—O(SO)OCH$_3$) |
| 46 | TMP | OEt | O | O | Ethoxysulfinyloxy (—O(SO)OCH$_2$CH$_3$) |
| 47 | TMP | OEt | O | O | n-Butoxysulfinyloxy (—O(SO)OCH$_2$CH$_2$CH$_2$CH$_3$) |
| 48 | TMP | OEt | O | O | Chlorosulfuryloxy (—O(SO$_2$)Cl) |
| 49 | TMP | OEt | O | O | Methoxysulfuryloxy (—O(SO$_2$)OCH$_3$) |
| 50 | TMP | OEt | O | O | Ethoxysulfuryloxy (—O(SO$_2$)OCH$_2$CH$_3$) |
| 51 | TMP | OEt | O | O | Methylsulfonyloxy (—O(SO$_2$)CH$_3$) |
| 52 | TMP | OEt | O | O | Trifluoromethylsulfonyloxy (—O(SO$_2$)CF$_3$) |
| 53 | TMP | OEt | O | O | Benzenesulfonyloxy (—O(SO$_2$)Ph) |
| 54 | TMP | OEt | O | O | p-Toluenesulfonyloxy (—O(SO$_2$)Ph-4-CH$_3$) |
| 55 | TMP | OEt | O | O | Dodecylbenzenesulfonyloxy |
| 56 | TMP | OEt | O | O | p-Bromobenzenesulfonyloxy (—O(SO$_2$)Ph-4-Br) |
| 57 | TMP | OEt | O | O | Diethyl(2-hydroxyethyl)ammonium |
| 58 | TMP | OEt | O | O | Benzyldiethylammonium |

-continued

| I- | R¹ | R² | Y | Z | FG |
|---|---|---|---|---|---|
| 59 | TMP | OEt | O | O | Tris(2-hydroxyethyl)ammonium |
| 60 | TMP | OEt | O | O | Dimethyl(2-hydroxyethyl)ammonium |
| 61 | TMP | OEt | O | O | Benzyldimethylammonium |
| 62 | TMP | OEt | O | O | Trimethylammonium |
| 63 | TMP | TMB | O | O | Cl |
| 64 | TMP | TMB | O | O | I |
| 65 | TMP | TMB | O | O | OCN |
| 66 | TMP | TMB | O | O | SCN |
| 67 | TMP | TMB | O | O | CN |
| 68 | TMP | TMB | O | O | Acetoxy (—O(CO)CH$_3$) |
| 69 | TMP | TMB | O | O | Benzoyloxy (—O(CO)Ph) |
| 70 | TMP | TMB | O | O | Formyloxy (—O(CO)H) |
| 71 | TMP | TMB | O | O | Methoxycarbonyloxy (—O(CO)OCH$_3$) |
| 72 | TMP | TMB | O | O | Ethoxycarbonyloxy (—O(CO)OCH$_2$CH$_3$) |
| 73 | TMP | TMB | O | O | n-Butoxycarbonyloxy (—O(CO)OCH$_2$CH$_2$CH$_2$CH$_3$) |
| 74 | TMP | TMB | O | O | Chlorocarbonyloxy (—O(CO)Cl) |
| 75 | TMP | TMB | O | O | Chlorosulfinyloxy (—O(SO)Cl) |
| 76 | TMP | TMB | O | O | Methoxysulfinyloxy (—O(SO)OCH$_3$) |
| 77 | TMP | TMB | O | O | Ethoxysulfinyloxy (—O(SO)OCH$_2$CH$_3$) |
| 78 | TMP | TMB | O | O | n-Butoxysulfinyloxy (—O(SO)OCH$_2$CH$_2$CH$_2$CH$_3$) |
| 79 | TMP | TMB | O | O | Chlorosulfuryloxy (—O(SO$_2$)Cl) |
| 80 | TMP | TMB | O | O | Methoxysulfuryloxy (—O(SO$_2$)OCH$_3$) |
| 81 | TMP | TMB | O | O | Ethoxysulfurylyoxy (—O(SO$_2$)OCH$_2$CH$_3$) |
| 82 | TMP | TMB | O | O | Methylsulfonyloxy (—O(SO$_2$)CH$_3$) |
| 83 | TMP | TMB | O | O | Trifluoromethylsulfonyloxy (—O(SO$_2$)CF$_3$) |
| 84 | TMP | TMB | O | O | Benzenesulfonyloxy (—O(SO$_2$)Ph) |
| 85 | TMP | TMB | O | O | p-Toluenesulfonyloxy (—O(SO$_2$)Ph-4-CH$_3$) |
| 86 | TMP | TMB | O | O | Dodecylbenzenesulfonyloxy |
| 87 | TMP | TMB | O | O | p-Bromobenzenesulfonyloxy (—O(SO$_2$)Ph-4-Br) |
| 88 | TMP | TMB | O | O | Diethyl(2-hydroxyethyl)ammonium |
| 89 | TMP | TMB | O | O | Benzyldiethylammonium |
| 90 | TMP | TMB | O | O | Tris(2-hydroxyethyl)ammonium |
| 91 | TMP | TMB | O | O | Dimethyl(2-hydroxyethyl)ammonium |
| 92 | TMP | TMB | O | O | Benzyldimethylammonium |
| 93 | TMP | TMB | O | O | Trimethylammonium |
| 94 | DMP | Ph | O | O | Cl |
| 95 | DMP | Ph | O | O | I |
| 96 | DMP | Ph | O | O | OCN |
| 97 | DMP | Ph | O | O | SCN |
| 98 | DMP | Ph | O | O | CN |
| 99 | DMP | Ph | O | O | Acetoxy (—O(CO)CH$_3$) |
| 100 | DMP | Ph | O | O | Benzoyloxy (—O(CO)Ph) |
| 101 | DMP | Ph | O | O | Formyloxy (—O(CO)H) |
| 102 | DMP | Ph | O | O | Methoxycarbonyloxy (—O(CO)OCH$_3$) |
| 103 | DMP | Ph | O | O | Ethoxycarbonyloxy (—O(CO)OCH$_2$CH$_3$) |
| 104 | DMP | Ph | O | O | n-Butoxycarbonyloxy (—O(CO)OCH$_2$CH$_2$CH$_2$CH$_3$) |
| 105 | DMP | Ph | O | O | Chlorocarbonyloxy (—O(CO)Cl) |
| 106 | DMP | Ph | O | O | Chlorosulfinyloxy (—O(SO)Cl) |
| 107 | DMP | Ph | O | O | Methoxysulfinyloxy (—O(SO)OCH$_3$) |
| 108 | DMP | Ph | O | O | Ethoxysulfinyloxy (—O(SO)OCH$_2$CH$_3$) |
| 109 | DMP | Ph | O | O | n-Butoxysulfinyloxy (—O(SO)OCH$_2$CH$_2$CH$_2$CH$_3$) |
| 110 | DMP | Ph | O | O | Chlorosulfuryloxy (—O(SO$_2$)Cl) |
| 111 | DMP | Ph | O | O | Methoxysulfuryloxy (—O(SO$_2$)OCH$_3$) |
| 112 | DMP | Ph | O | O | Ethoxysulfurylyoxy (—O(SO$_2$)OCH$_2$CH$_3$) |
| 113 | DMP | Ph | O | O | Methylsulfonyloxy (—O(SO$_2$)CH$_3$) |
| 114 | DMP | Ph | O | O | Trifluoromethylsulfonyloxy (—O(SO$_2$)CF$_3$) |
| 115 | DMP | Ph | O | O | Benzenesulfonyloxy (—O(SO$_2$)Ph) |
| 116 | DMP | Ph | O | O | p-Toluenesulfonyloxy (—O(SO$_2$)Ph-4-CH$_3$) |
| 117 | DMP | Ph | O | O | Dodecylbenzenesulfonyloxy |
| 118 | DMP | Ph | O | O | p-Bromobenzenesulfonyloxy (—O(SO$_2$)Ph-4-Br) |
| 119 | DMP | Ph | O | O | Diethyl(2-hydroxyethyl)ammonium |
| 120 | DMP | Ph | O | O | Benzyldiethylammonium |
| 121 | DMP | Ph | O | O | Tris(2-hydroxyethyl)ammonium |
| 122 | DMP | Ph | O | O | Dimethyl(2-hydroxyethyl)ammonium |
| 123 | DMP | Ph | O | O | Benzyldimethylammonium |
| 124 | DMP | Ph | O | O | Trimethylammonium |
| 125 | DMP | OEt | O | O | Cl |
| 126 | DMP | OEt | O | O | I |
| 127 | DMP | OEt | O | O | OCN |
| 128 | DMP | OEt | O | O | SCN |
| 129 | DMP | OEt | O | O | CN |
| 130 | DMP | OEt | O | O | Acetoxy (—O(CO)CH$_3$) |
| 131 | DMP | OEt | O | O | Benzoyloxy (—O(CO)Ph) |
| 132 | DMP | OEt | O | O | Formyloxy (—O(CO)H) |
| 133 | DMP | OEt | O | O | Methoxycarbonyloxy (—O(CO)OCH$_3$) |

-continued

| I- | R¹ | R² | Y | Z | FG |
|---|---|---|---|---|---|
| 134 | DMP | OEt | O | O | Ethoxycarbonyloxy (—O(CO)OCH₂CH₃) |
| 135 | DMP | OEt | O | O | n-Butoxycarbonyloxy (—O(CO)OCH₂CH₂CH₂CH₃) |
| 136 | DMP | OEt | O | O | Chlorocarbonyloxy (—O(CO)Cl) |
| 137 | DMP | OEt | O | O | Chlorosulfinyloxy (—O(SO)Cl) |
| 138 | DMP | OEt | O | O | Methoxysulfinyloxy (—O(SO)OCH₃) |
| 139 | DMP | OEt | O | O | Ethoxysulfinyloxy (—O(SO)OCH₂CH₃) |
| 140 | DMP | OEt | O | O | n-Butoxysulfinyloxy (—O(SO)OCH₂CH₂CH₂CH₃) |
| 141 | DMP | OEt | O | O | Chlorosulfuryloxy (—O(SO₂)Cl) |
| 142 | DMP | OEt | O | O | Methoxysulfuryloxy (—O(SO₂)OCH₃) |
| 143 | DMP | OEt | O | O | Ethoxysulfuryloxy (—O(SO₂)OCH₂CH₃) |
| 144 | DMP | OEt | O | O | Methylsulfonyloxy (—O(SO₂)CH₃) |
| 145 | DMP | OEt | O | O | Trifluoromethylsulfonyloxy (—O(SO₂)CF₃) |
| 146 | DMP | OEt | O | O | Benzenesulfonyloxy (—O(SO₂)Ph) |
| 147 | DMP | OEt | O | O | p-Toluenesulfonyloxy (—O(SO₂)Ph-4-CH₃) |
| 148 | DMP | OEt | O | O | Dodecylbenzenesulfonyloxy |
| 149 | DMP | OEt | O | O | p-Bromobenzenesulfonyloxy (—O(SO₂)Ph-4-Br) |
| 150 | DMP | OEt | O | O | Diethyl(2-hydroxyethyl)ammonium |
| 151 | DMP | OEt | O | O | Benzyldiethylammonium |
| 152 | DMP | OEt | O | O | Tris(2-hydroxyethyl)ammonium |
| 153 | DMP | OEt | O | O | Dimethyl(2-hydroxyethyl)ammonium |
| 154 | DMP | OEt | O | O | Benzyldimethylammonium |
| 155 | DMP | OEt | O | O | Trimethylammonium |
| 156 | DMP | TMB | O | O | Cl |
| 157 | DMP | TMB | O | O | I |
| 158 | DMP | TMB | O | O | OCN |
| 159 | DMP | TMB | O | O | SCN |
| 160 | DMP | TMB | O | O | CN |
| 161 | DMP | TMB | O | O | Acetoxy (—O(CO)CH₃) |
| 162 | DMP | TMB | O | O | Benzoyloxy (—O(CO)Ph) |
| 163 | DMP | TMB | O | O | Formyloxy (—O(CO)H) |
| 164 | DMP | TMB | O | O | Methoxycarbonyloxy (—O(CO)OCH₃) |
| 165 | DMP | TMB | O | O | Ethoxycarbonyloxy (—O(CO)OCH₂CH₃) |
| 166 | DMP | TMB | O | O | n-Butoxycarbonyloxy (—O(CO)OCH₂CH₂CH₂CH₃) |
| 167 | DMP | TMB | O | O | Chlorocarbonyloxy (—O(CO)Cl) |
| 168 | DMP | TMB | O | O | Chlorosulfinyloxy (—O(SO)Cl) |
| 169 | DMP | TMB | O | O | Methoxysulfinyloxy (—O(SO)OCH₃) |
| 170 | DMP | TMB | O | O | Ethoxysulfinyloxy (—O(SO)OCH₂CH₃) |
| 171 | DMP | TMB | O | O | n-Butoxysulfinyloxy (—O(SO)OCH₂CH₂CH₂CH₃) |
| 172 | DMP | TMB | O | O | Chlorosulfuryloxy (—O(SO₂)Cl) |
| 173 | DMP | TMB | O | O | Methoxysulfuryloxy (—O(SO₂)OCH₃) |
| 174 | DMP | TMB | O | O | Ethoxysulfuryloxy (—O(SO₂)OCH₂CH₃) |
| 175 | DMP | TMB | O | O | Methylsulfonyloxy (—O(SO₂)CH₃) |
| 176 | DMP | TMB | O | O | Trifluoromethylsulfonyloxy (—O(SO₂)CF₃) |
| 177 | DMP | TMB | O | O | Benzenesulfonyloxy (—O(SO₂)Ph) |
| 178 | DMP | TMB | O | O | p-Toluenesulfonyloxy (—O(SO₂)Ph-4-CH₃) |
| 179 | DMP | TMB | O | O | Dodecylbenzenesulfonyloxy |
| 180 | DMP | TMB | O | O | p-Bromobenzenesulfonyloxy (—O(SO₂)Ph-4-Br) |
| 181 | DMP | TMB | O | O | Diethyl(2-hydroxyethyl)ammonium |
| 182 | DMP | TMB | O | O | Benzyldiethylammonium |
| 183 | DMP | TMB | O | O | Tris(2-hydroxyethyl)ammonium |
| 184 | DMP | TMB | O | O | Dimethyl(2-hydroxyethyl)ammonium |
| 185 | DMP | TMB | O | O | Benzyldimethylammonium |
| 186 | DMP | TMB | O | O | Trimethylammonium |
| 187 | DMOP | Ph | O | O | Cl |
| 188 | DMOP | Ph | O | O | I |
| 189 | DMOP | Ph | O | O | OCN |
| 190 | DMOP | Ph | O | O | SCN |
| 191 | DMOP | Ph | O | O | CN |
| 192 | DMOP | Ph | O | O | Acetoxy (—O(CO)CH₃) |
| 193 | DMOP | Ph | O | O | Benzoyloxy (—O(CO)Ph) |
| 194 | DMOP | Ph | O | O | Formyloxy (—O(CO)H) |
| 195 | DMOP | Ph | O | O | Methoxycarbonyloxy (—O(CO)OCH₃) |
| 196 | DMOP | Ph | O | O | Ethoxycarbonyloxy (—O(CO)OCH₂CH₃) |
| 197 | DMOP | Ph | O | O | n-Butoxycarbonyloxy (—O(CO)OCH₂CH₂CH₂CH₃) |
| 198 | DMOP | Ph | O | O | Chlorocarbonyloxy (—O(CO)Cl) |
| 199 | DMOP | Ph | O | O | Chlorosulfinyloxy (—O(SO)Cl) |
| 200 | DMOP | Ph | O | O | Methoxysulfinyloxy (—O(SO)OCH₃) |
| 201 | DMOP | Ph | O | O | Ethoxysulfinyloxy (—O(SO)OCH₂CH₃) |
| 202 | DMOP | Ph | O | O | n-Butoxysulfinyloxy (—O(SO)OCH₂CH₂CH₂CH₃) |
| 203 | DMOP | Ph | O | O | Chlorosulfuryloxy (—O(SO₂)Cl) |
| 204 | DMOP | Ph | O | O | Methoxysulfuryloxy (—O(SO₂)OCH₃) |
| 205 | DMOP | Ph | O | O | Ethoxysulfuryloxy (—O(SO₂)OCH₂CH₃) |
| 206 | DMOP | Ph | O | O | Methylsulfonyloxy (—O(SO₂)CH₃) |
| 207 | DMOP | Ph | O | O | Trifluoromethylsulfonyloxy (—O(SO₂)CF₃) |
| 208 | DMOP | Ph | O | O | Benzenesulfonyloxy (—O(SO₂)Ph) |

-continued

| I- | R¹ | R² | Y | Z | FG |
|---|---|---|---|---|---|
| 209 | DMOP | Ph | O | O | p-Toluenesulfonyloxy (—O(SO₂)Ph-4-CH₃) |
| 210 | DMOP | Ph | O | O | Dodecylbenzenesulfonyloxy |
| 211 | DMOP | Ph | O | O | p-Bromobenzenesulfonyloxy (—O(SO₂)Ph-4-Br) |
| 212 | DMOP | Ph | O | O | Diethyl(2-hydroxyethyl)ammonium |
| 213 | DMOP | Ph | O | O | Benzyldiethylammonium |
| 214 | DMOP | Ph | O | O | Tris(2-hydroxyethyl)ammonium |
| 215 | DMOP | Ph | O | O | Dimethyl(2-hydroxyethyl)ammonium |
| 216 | DMOP | Ph | O | O | Benzyldimethylammonium |
| 217 | DMOP | Ph | O | O | Trimethylammonium |
| 218 | DMOP | OEt | O | O | Cl |
| 219 | DMOP | OEt | O | O | I |
| 220 | DMOP | OEt | O | O | OCN |
| 221 | DMOP | OEt | O | O | SCN |
| 222 | DMOP | OEt | O | O | CN |
| 223 | DMOP | OEt | O | O | Acetoxy (—O(CO)CH₃) |
| 224 | DMOP | OEt | O | O | Benzoyloxy (—O(CO)Ph) |
| 225 | DMOP | OEt | O | O | Formyloxy (—O(CO)H) |
| 226 | DMOP | OEt | O | O | Methoxycarbonyloxy (—O(CO)OCH₃) |
| 227 | DMOP | OEt | O | O | Ethoxycarbonyloxy (—O(CO)OCH₂CH₃) |
| 228 | DMOP | OEt | O | O | n-Butoxycarbonyloxy (—O(CO)OCH₂CH₂CH₂CH₃) |
| 229 | DMOP | OEt | O | O | Chlorocarbonyloxy (—O(CO)Cl) |
| 230 | DMOP | OEt | O | O | Chlorosulfinyloxy (—O(SO)Cl) |
| 231 | DMOP | OEt | O | O | Methoxysulfinyloxy (—O(SO)OCH₃) |
| 232 | DMOP | OEt | O | O | Ethoxysulfinyloxy (—O(SO)OCH₂CH₃) |
| 233 | DMOP | OEt | O | O | n-Butoxysulfinyloxy (—O(SO)OCH₂CH₂CH₂CH₃) |
| 234 | DMOP | OEt | O | O | Chlorosulfurylyoxy (—O(SO₂)Cl) |
| 235 | DMOP | OEt | O | O | Methoxysulfurylyoxy (—O(SO₂)OCH₃) |
| 236 | DMOP | OEt | O | O | Ethoxysulfurylyoxy (—O(SO₂)OCH₂CH₃) |
| 237 | DMOP | OEt | O | O | Methylsulfonyloxy (—O(SO₂)CH₃) |
| 238 | DMOP | OEt | O | O | Trifluoromethylsulfonyloxy (—O(SO₂)CF₃) |
| 239 | DMOP | OEt | O | O | Benzenesulfonyloxy (—O(SO₂)Ph) |
| 240 | DMOP | OEt | O | O | p-Toluenesulfonyloxy (—O(SO₂)Ph-4-CH₃) |
| 241 | DMOP | OEt | O | O | Dodecylbenzenesulfonyloxy |
| 242 | DMOP | OEt | O | O | p-Bromobenzenesulfonyloxy (—O(SO₂)Ph-4-Br) |
| 243 | DMOP | OEt | O | O | Diethyl(2-hydroxyethyl)ammonium |
| 244 | DMOP | OEt | O | O | Benzyldiethylammonium |
| 245 | DMOP | OEt | O | O | Tris(2-hydroxyethyl)ammonium |
| 246 | DMOP | OEt | O | O | Dimethyl(2-hydroxyethyl)ammonium |
| 247 | DMOP | OEt | O | O | Benzyldimethylammonium |
| 248 | DMOP | OEt | O | O | Trimethylammonium |
| 249 | DMOP | TMB | O | O | Cl |
| 250 | DMOP | TMB | O | O | I |
| 251 | DMOP | TMB | O | O | OCN |
| 252 | DMOP | TMB | O | O | SCN |
| 253 | DMOP | TMB | O | O | CN |
| 254 | DMOP | TMB | O | O | Acetoxy (—O(CO)CH₃) |
| 255 | DMOP | TMB | O | O | Benzoyloxy (—O(CO)Ph) |
| 256 | DMOP | TMB | O | O | Formyloxy (—O(CO)H) |
| 257 | DMOP | TMB | O | O | Methoxycarbonyloxy (—O(CO)OCH₃) |
| 258 | DMOP | TMB | O | O | Ethoxycarbonyloxy (—O(CO)OCH₂CH₃) |
| 259 | DMOP | TMB | O | O | n-Butoxycarbonyloxy (—O(CO)OCH₂CH₂CH₂CH₃) |
| 260 | DMOP | TMB | O | O | Chlorocarbonyloxy (—O(CO)Cl) |
| 261 | DMOP | TMB | O | O | Chlorosulfinyloxy (—O(SO)Cl) |
| 262 | DMOP | TMB | O | O | Methoxysulfinyloxy (—O(SO)OCH₃) |
| 263 | DMOP | TMB | O | O | Ethoxysulfinyloxy (—O(SO)OCH₂CH₃) |
| 264 | DMOP | TMB | O | O | n-Butoxysulfinyloxy (—O(SO)OCH₂CH₂CH₂CH₃) |
| 265 | DMOP | TMB | O | O | Chlorosulfurylyoxy (—O(SO₂)Cl) |
| 266 | DMOP | TMB | O | O | Methoxysulfurylyoxy (—O(SO₂)OCH₃) |
| 267 | DMOP | TMB | O | O | Ethoxysulfurylyoxy (—O(SO₂)OCH₂CH₃) |
| 268 | DMOP | TMB | O | O | Methylsulfonyloxy (—O(SO₂)CH₃) |
| 269 | DMOP | TMB | O | O | Trifluoromethylsulfonyloxy (—O(SO₂)CF₃) |
| 270 | DMOP | TMB | O | O | Benzenesulfonyloxy (—O(SO₂)Ph) |
| 271 | DMOP | TMB | O | O | p-Toluenesulfonyloxy (—O(SO₂)Ph-4-CH₃) |
| 272 | DMOP | TMB | O | O | Dodecylbenzenesulfonyloxy |
| 273 | DMOP | TMB | O | O | p-Bromobenzenesulfonyloxy (—O(SO₂)Ph-4-Br) |
| 274 | DMOP | TMB | O | O | Diethyl(2-hydroxyethyl)ammonium |
| 275 | DMOP | TMB | O | O | Benzyldimethylammonium |
| 276 | DMOP | TMB | O | O | Tris(2-hydroxyethyl)ammonium |
| 277 | DMOP | TMB | O | O | Dimethyl(2-hydroxyethyl)ammonium |
| 278 | DMOP | TMB | O | O | Benzyldimethylammonium |
| 279 | DMOP | TMB | O | O | Trimethylammonium |
| 280 | DCP | Ph | O | O | Cl |
| 281 | DCP | Ph | O | O | I |
| 282 | DCP | Ph | O | O | OCN |

-continued

| I- | R¹ | R² | Y | Z | FG |
|---|---|---|---|---|---|
| 283 | DCP | Ph | O | O | SCN |
| 284 | DCP | Ph | O | O | CN |
| 285 | DCP | Ph | O | O | Acetoxy (—O(CO)CH$_3$) |
| 286 | DCP | Ph | O | O | Benzoyloxy (—O(CO)Ph) |
| 287 | DCP | Ph | O | O | Formyloxy (—O(CO)H) |
| 288 | DCP | Ph | O | O | Methoxycarbonyloxy (—O(CO)OCH$_3$) |
| 289 | DCP | Ph | O | O | Ethoxycarbonyloxy (—O(CO)OCH$_2$CH$_3$) |
| 290 | DCP | Ph | O | O | n-Butoxycarbonyloxy (—O(CO)OCH$_2$CH$_2$CH$_2$CH$_3$) |
| 291 | DCP | Ph | O | O | Chlorocarbonyloxy (—O(CO)Cl) |
| 292 | DCP | Ph | O | O | Chlorosulfinyloxy (—O(SO)Cl) |
| 293 | DCP | Ph | O | O | Methoxysulfinyloxy (—O(SO)OCH$_3$) |
| 294 | DCP | Ph | O | O | Ethoxysulfinyloxy (—O(SO)OCH$_2$CH$_3$) |
| 295 | DCP | Ph | O | O | n-Butoxysulfinyloxy (—O(SO)OCH$_2$CH$_2$CH$_2$CH$_3$) |
| 296 | DCP | Ph | O | O | Chlorosulfuryloxy (—O(SO$_2$)Cl) |
| 297 | DCP | Ph | O | O | Methoxysulfuryloxy (—O(SO$_2$)OCH$_3$) |
| 298 | DCP | Ph | O | O | Ethoxysulfuryloxy (—O(SO$_2$)OCH$_2$CH$_3$) |
| 299 | DCP | Ph | O | O | Methylsulfonyloxy (—O(SO$_2$)CH$_3$) |
| 300 | DCP | Ph | O | O | Trifluoromethylsulfonyloxy (—O(SO$_2$)CF$_3$) |
| 301 | DCP | Ph | O | O | Benzenesulfonyloxy (—O(SO$_2$)Ph) |
| 302 | DCP | Ph | O | O | p-Toluenesulfonyloxy (—O(SO$_2$)Ph-4-CH$_3$) |
| 303 | DCP | Ph | O | O | Dodecylbenzenesulfonyloxy |
| 304 | DCP | Ph | O | O | p-Bromobenzenesulfonyloxy (—O(SO$_2$)Ph-4-Br) |
| 305 | DCP | Ph | O | O | Diethyl(2-hydroxyethyl)ammonium |
| 306 | DCP | Ph | O | O | Benzyldiethylammonium |
| 307 | DCP | Ph | O | O | Tris(2-hydroxyethyl)ammonium |
| 308 | DCP | Ph | O | O | Dimethyl(2-hydroxyethyl)ammonium |
| 309 | DCP | Ph | O | O | Benzyldimethylammonium |
| 310 | DCP | Ph | O | O | Trimethylammonium |
| 311 | DCP | OEt | O | O | Cl |
| 312 | DCP | OEt | O | O | I |
| 313 | DCP | OEt | O | O | OCN |
| 314 | DCP | OEt | O | O | SCN |
| 315 | DCP | OEt | O | O | CN |
| 316 | DCP | OEt | O | O | Acetoxy (—O(CO)CH$_3$) |
| 317 | DCP | OEt | O | O | Benzoyloxy (—O(CO)Ph) |
| 318 | DCP | OEt | O | O | Formyloxy (—O(CO)H) |
| 319 | DCP | OEt | O | O | Methoxycarbonyloxy (—O(CO)OCH$_3$) |
| 320 | DCP | OEt | O | O | Ethoxycarbonyloxy (—O(CO)OCH$_2$CH$_3$) |
| 321 | DCP | OEt | O | O | n-Butoxycarbonyloxy (—O(CO)OCH$_2$CH$_2$CH$_2$CH$_3$) |
| 322 | DCP | OEt | O | O | Chlorocarbonyloxy (—O(CO)Cl) |
| 323 | DCP | OEt | O | O | Chlorosulfinyloxy (—O(SO)Cl) |
| 324 | DCP | OEt | O | O | Methoxysulfinyloxy (—O(SO)OCH$_3$) |
| 325 | DCP | OEt | O | O | Ethoxysulfinyloxy (—O(SO)OCH$_2$CH$_3$) |
| 326 | DCP | OEt | O | O | n-Butoxysulfinyloxy (—O(SO)OCH$_2$CH$_2$CH$_2$CH$_3$) |
| 327 | DCP | OEt | O | O | Chlorosulfuryloxy (—O(SO$_2$)Cl) |
| 328 | DCP | OEt | O | O | Methoxysulfuryloxy (—O(SO$_2$)OCH$_3$) |
| 329 | DCP | OEt | O | O | Ethoxysulfuryloxy (—O(SO$_2$)OCH$_2$CH$_3$) |
| 330 | DCP | OEt | O | O | Methylsulfonyloxy (—O(SO$_2$)CH$_3$) |
| 331 | DCP | OEt | O | O | Trifluoromethylsulfonyloxy (—O(SO$_2$)CF$_3$) |
| 332 | DCP | OEt | O | O | Benzenesulfonyloxy (—O(SO$_2$)Ph) |
| 333 | DCP | OEt | O | O | p-Toluenesulfonyloxy (—O(SO$_2$)Ph-4-CH$_3$) |
| 334 | DCP | OEt | O | O | Dodecylbenzenesulfonyloxy |
| 335 | DCP | OEt | O | O | p-Bromobenzenesulfonyloxy (—O(SO$_2$)Ph-4-Br) |
| 336 | DCP | OEt | O | O | Diethyl(2-hydroxyethyl)ammonium |
| 337 | DCP | OEt | O | O | Benzyldiethylammonium |
| 338 | DCP | OEt | O | O | Tris(2-hydroxyethyl)ammonium |
| 339 | DCP | OEt | O | O | Dimethyl(2-hydroxyethyl)ammonium |
| 340 | DCP | OEt | O | O | Benzyldimethylammonium |
| 341 | DCP | OEt | O | O | Trimethylammonium |
| 342 | DCP | TMB | O | O | Cl |
| 343 | DCP | TMB | O | O | I |
| 344 | DCP | TMB | O | O | OCN |
| 345 | DCP | TMB | O | O | SCN |
| 346 | DCP | TMB | O | O | CN |
| 347 | DCP | TMB | O | O | Acetoxy (—O(CO)CH$_3$) |
| 348 | DCP | TMB | O | O | Benzoyloxy (—O(CO)Ph) |
| 349 | DCP | TMB | O | O | Formyloxy (—O(CO)H) |
| 350 | DCP | TMB | O | O | Methoxycarbonyloxy (—O(CO)OCH$_3$) |
| 351 | DCP | TMB | O | O | Ethoxycarbonyloxy (—O(CO)OCH$_2$CH$_3$) |
| 352 | DCP | TMB | O | O | n-Butoxycarbonyloxy (—O(CO)OCH$_2$CH$_2$CH$_2$CH$_3$) |
| 353 | DCP | TMB | O | O | Chlorocarbonyloxy (—O(CO)Cl) |
| 354 | DCP | TMB | O | O | Chlorosulfinyloxy (—O(SO)Cl) |
| 355 | DCP | TMB | O | O | Methoxysulfinyloxy (—O(SO)OCH$_3$) |
| 356 | DCP | TMB | O | O | Ethoxysulfinyloxy (—O(SO)OCH$_2$CH$_3$) |
| 357 | DCP | TMB | O | O | n-Butoxysulfinyloxy (—O(SO)OCH$_2$CH$_2$CH$_2$CH$_3$) |

| I- | R¹ | R² | Y | Z | FG |
|---|---|---|---|---|---|
| 358 | DCP | TMB | O | O | Chlorosulfuryloxy (—O(SO₂)Cl) |
| 359 | DCP | TMB | O | O | Methoxysulfuryloxy (—O(SO₂)OCH₃) |
| 360 | DCP | TMB | O | O | Ethoxysulfuryloxy (—O(SO₂)OCH₂CH₃) |
| 361 | DCP | TMB | O | O | Methylsulfonyloxy (—O(SO₂)CH₃) |
| 362 | DCP | TMB | O | O | Trifluoromethylsulfonyloxy (—O(SO₂)CF₃) |
| 363 | DCP | TMB | O | O | Benzenesulfonyloxy (—O(SO₂)Ph) |
| 364 | DCP | TMB | O | O | p-Toluenesulfonyloxy (—O(SO₂)Ph-4-CH₃) |
| 365 | DCP | TMB | O | O | Dodecylbenzenesulfonyloxy |
| 366 | DCP | TMB | O | O | p-Bromobenzenesulfonyloxy (—O(SO₂)Ph-4-Br) |
| 367 | DCP | TMB | O | O | Diethyl(2-hydroxyethyl)ammonium |
| 368 | DCP | TMB | O | O | Benzyldiethylammonium |
| 369 | DCP | TMB | O | O | Tris(2-hydroxyethyl)ammonium |
| 370 | DCP | TMB | O | O | Dimethyl(2-hydroxyethyl)ammonium |
| 371 | DCP | TMB | O | O | Benzyldimethylammonium |
| 372 | DCP | TMB | O | O | Trimethylammonium |

TMP: 2,4,6-trimethyl-1-phenyl
DMP: 2,6-dimethyl-1-phenyl
DMOP: 2,6-dimethoxy-1-phenyl
DCP: 2,6-dichloro-1-phenyl
TMB: 2,4,6-trimethylbenzoyl
Ph: phenyl
EtO: ethoxy As stated above, preference is also given to the species from the table in which $R^2$ is 4-methylphenyl, 4-methoxyphenyl, 4-chlorophenyl, methoxy, n-propoxy, iso-propoxy, n-butoxy, sec-butoxy, iso-butoxy or tert-butoxy.

As stated above, preference is also given to the species from the table in which $R^1$ is ortho-substituted, for example 2-methylphenyl, 2-methoxyphenyl or 2-chlorophenyl.

The acyl- and bisacylphosphine derivatives (I) according to the invention can be prepared by a process in which a substance of the formula (II)

where $R^1$, $R^2$, Y and Z are as defined above, and

X is hydrogen or a cation, is reacted with at least one agent which converts the —OX group into an —FG group.

Cations here can be, for example, those as listed in EP-A 62 839, i.e. equivalents of a cation from main group 1 to 3 of the Periodic Table having a molecular weight of less than 138, or ammonium ions derived from quaternary ammonium ions or triethylenediammonium ions.

Agents which convert the —OX group into the —FG group are known per se to the person skilled in the art. Examples which may be mentioned are phosgene (COCl₂), thionyl chloride (SOCl₂), sulfuryl chloride (SO₂Cl₂), phosphorus trichloride (PCl₃), phosphorus oxide trichloride (POCl₃), phosphorus pentachloride (PCl₅), oxalyl chloride ((COCl)₂), hydrogen chloride (HCl), chlorine gas (Cl₂), N-chloro compounds, for example N-chlorosuccinimide, alkali metal fluorides, cobalt(III) fluoride, halogen fluorides, antimony fluorides, molybdenum fluoride, hydrogen fluoride, hydrogen fluoride/pyridine mixtures, xenon fluorides and other noble-gas compounds, gaseous fluorine, sulfur tetrafluoride, iodine, iodine monochloride, phosphorus triiodide, acid iodides, N-iodosuccinimide, N-iodoacetamide, cyanogen chloride (ClCN), cyanuric chloride (2,4,6-trichloro-1,3,5-triazine, C₃Cl₃N₃), acid chlorides (R⁵(CO)Cl), esters or anhydrides (R⁵(CO)₂O), carbonic acid chlorides (R⁵O(CO)Cl), carbonates ((R⁵O)₂(CO)), sulfonic acid chlorides (R⁵SO₂Cl) or sulfonic anhydrides ((R⁵SO₂)₂O).

If, furthermore, it is intended to prepare a compound where FG=Br, suitable agents can be, for example: bromine, alkali metal hypobromite, bromine iodide, cyanogen bromide, PBr₃, PBr₅, POBr₃, SOBr₂, N-bromosuccinimide, N-bromoacetamide and 1,3-dibromo-5,5-dimethylhydantoin.

If the leaving group FG also contains a reactive center, as in the case of the reaction with phosgene, thionyl chloride, sulfuryl chloride, oxalyl chloride, etc., it is possible to react this reactive center again, for example with an alcohol R⁵OH, so that —(CO)Cl, —(SO)Cl, —(SO₂)Cl groups, etc., are converted into —(CO)OR⁵, —(SO)OR⁵ or —(SO₂)OR⁵ groups respectively.

It is furthermore also possible, instead of an —OX group, to convert an —NH₂, —NHR⁶ or —NR⁶R⁷ group into an —N⁺R⁶R⁷R⁸ group by quaternization. This is possible, for example, by reaction with methyl chloride, methyl bromide, methyl iodide, ethyl chloride, ethyl bromide, ethyl iodide, benzyl chloride, dimethyl sulfate, diethyl sulfate, dimethyl carbonate, dibutyl carbonate, ethylene oxide or propylene oxide.

The performance of the reaction for conversion of the —OX group into the —FG group using the above-mentioned agents is known per se to the person skilled in the art and is described, for example, in Organikum—Organisch-chemisches Grundpraktikum, 17th Edition, Berlin, 1988, VEB Deutscher Verlag der Wissenschaften, on pages 189 to 191 (thionyl chloride, phosphorus chlorides and iodine/phosphorus) and 559 (p-toluenesulfonic acid esters), or in Houben-Weyl, Methoden der Organischen Chemie, 4th Edition, 1955, Thieme Verlag, Stuttgart, Ed. Eugen Müller, Volume 9, pages 663 to 668 and 671 to 673 (sulfonic acid esters).

For the reaction with thionyl chloride or R⁵(SO)Cl, the substrate to be reacted, if desired dissolved in a suitable solvent, for example benzene, toluene, xylene, tetrahydrofuran, hexane, heptane, pentane or petroleum ether, is usually initially introduced in the presence of from 0.9 to 1.5 mol equivalents of an acid scavenger, such as pyridine or a tertiary amine, for example triethylamine, tributylamine, benzyldimethylamine, dimethylaminopyridine, etc., at temperatures between 0° C. and 100° C., preferably between 10° C. and 80° C., and the agent is added with vigorous mixing over a period of from a few minutes to several hours, preferably from 10 to 300 minutes, particularly preferably from 30 to 180 minutes. Stirring can be continued if desired, for example for from 30 to 600 minutes, preferably from 60 to 300 minutes, during which the reaction temperature can slowly be raised in steps.

The resultant reaction product can be processed further in crude or purified form.

If further use in pure form is desired, the product can be purified, for example, by crystallization and solid/liquid separation or by distillation or rectification under reduced pressure.

The yields are generally greater than 75%, usually greater than 80% and frequently greater than 90%.

For the preparation of a group FG=Cl, preference is given to the use of phosgene, thionyl chloride or sulfuryl chloride, particularly preferably phosgene or thionyl chloride and in particular thionyl chloride.

For the preparation of a group FG=OSO$_2$R$^5$, preference is given to the use of R$^5$SO$_2$Cl or (R$^5$SO$_2$)$_2$O, particularly preferably R$^5$SO$_2$Cl.

The compounds of the formula (II) can be obtained as described in EP-A 62 839: a phosphinic acid ester (III), preferably a methyl, ethyl or n-butyl ester, prepared, for example, as mentioned at the outset, can be reacted with a metal halide (MeHal), for example LiCl, LiBr, LiI, NaCl, NaBr, NaI, KCl, KBr or KI, to give the compound (II), where X corresponds to the metal (Me) used. Acidification, for example using sulfuric acid, hydrochloric acid, phosphoric acid, nitric acid or sulfonic acids, or metal exchange with ion exchangers gives the compound (II) where X=H.

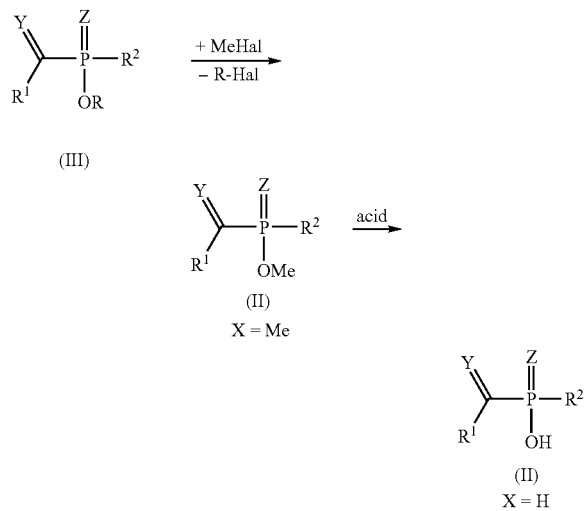

The present invention furthermore relates to a novel process for the preparation of compounds of the formula (II) where X=H in which compounds of the formula (III) are reacted with a halide which is a constituent of an ionic liquid.

The term ionic liquids here is taken to mean ionic compounds which are liquid under the reaction conditions and/or work-up conditions. The melting points of the preferred ionic liquids are generally below 160° C., particularly preferably below 100° C. and very particularly preferably below 80° C.

In the formula (III), R is as defined above for C$_1$-C$_{18}$-alkyl which is unsubstituted or substituted by aryl, alkyl, aryloxy, alkoxy, heteroatoms and/or heterocyclic radicals, preferably methyl, ethyl or n-butyl. R$^1$, R$^2$, Y and Z are as defined above.

The term halides here is taken to mean fluoride, chloride, bromide or iodide, preferably bromide or chloride and particularly preferably chloride.

Compounds of this type which can be employed as bases can contain phosphorus, sulfur or nitrogen atoms, for example at least one nitrogen atom, preferably from one to ten nitrogen atoms, particularly preferably from one to five nitrogen atoms, very particularly preferably from one to three nitrogen atoms and in particular one or two nitrogen atoms. If desired, further heteroatoms, for example oxygen, sulfur, phosphorus or halogen atoms, may also be present.

Preference is given to compounds which contain at least one five- to six-membered heterocyclic radical which contains at least one nitrogen atom and, if desired, an oxygen or sulfur atom, particularly preferably compounds which contain at least one five- to six-membered heterocyclic radical which contains one, two or three nitrogen atoms or one nitrogen atom and one oxygen atom, very particularly preferably those containing two nitrogen atoms.

Particularly preferred compounds are those which have a molecular weight of less than 1000 g/mol, very particularly preferably less than 500 g/mol and in particular less than 250 g/mol.

Particular preference is given to pyridines, pyridazines, pyrimidines, pyrazines, imidazoles, 1H-pyrazoles, 3H-pyrazoles, 4H-pyrazoles, 1-pyrazolines, 2-pyrazolines, 3-pyrazolines, imidazolines, thiazoles, oxazoles, 1,2,4-triazoles or 1,2,3-triazoles, of which the pyridines and imidazoles are preferred.

The very particularly preferred bases are 3-chloropyridine, 4-dimethylaminopyridine, 2-ethyl-4-aminopyridine, 2-methylpyridine, 2-ethylpyridine, 2-ethyl-6-methylpyridine, quinoline, isoquinoline, pyridine, 1-C$_1$-C$_4$-alkylimidazole, 1-methylimidazole, 1,2-dimethylimidazole, 1-n-butylimidazole, 1,4,5-trimethylimidazole, 1,4-dimethylimidazole, imidazole, 2-methylimidazole, 1-butyl-2-methylimidazole, 4-methylimidazole, 1-n-pentylimidazole, 1-n-hexylimidazole, 1-n-octylimidazole, 1-(2'-aminoethyl)imidazole, 2-ethyl-4-methylimidazole, 1-vinylimidazole, 2-ethylimidazole, 1-(2'-cyanoethyl)imidazole and benzotriazole.

Particular preference is given to 1-n-butylimidazole, 1-methylimidazole, 2-methylpyridine and 2-ethylpyridine.

To this end, the compound of the formula (III) is reacted with a halide dissolved in an ionic liquid, giving the salt of the said base with the acid (III) where X=H.

This generally requires temperatures of 40-160° C., preferably 50-150° C., particularly preferably 60-140° C., very particularly preferably 80-130° C. and in particular 90-120° C.

The reaction is preferably carried out in the presence of a gas which is inert under the reaction conditions; this is particularly preferably passed through the reaction mixture.

In a further embodiment, a slight reduced pressure is applied, for example 200-900 mbar, preferably 300-800 mbar and particularly preferably 500-750 mbar, in order to simplify separation of the alkyl halide formed.

The reaction mixture can subsequently be diluted with water and the acid (III) liberated using a suitable strong acid, for example sulfuric acid, hydrochloric acid, hydrobromic acid, nitric acid, formic acid or acetic acid, preferably with the strong acid which corresponds to the halide employed.

The acid (III) where X=H can subsequently be separated off by solid-liquid or liquid-liquid separation and, if necessary, purified further.

The acyl- and bisacylphosphine derivatives according to the invention can be used as photoinitiators for the radiation curing of photopolymerizable compositions, for example coating compositions, surface coatings, printing inks, recording materials, aqueous solutions, dispersions and emulsions.

The photoinitiators according to the invention can of course also be used in the form of a mixture with other photoinitiators. These can be, for example, photoinitiators known to the person skilled in the art, for example those mentioned in "Advances in Polymer Science", Volume 14, Springer Berlin, 1974, or in K. K. Dietliker, Chemistry and Technology of UV- and EB-Formulation for Coatings, Inks and Paints, Volume 3; Photoinitiators for Free Radical and Cationic Polymerization, P. K. T. Oldring (Eds), SITA Technology Ltd, London.

Suitable are, for example, mono- or bisacylphosphine oxides as described, for example, in EP-A 7 508, EP-A 57 474, DE-A 196 18 720, EP-A 495 751 or EP-A 615 980, for example 2,4,6-trimethylbenzoyldiphenylphosphine oxide (Lucirin® TPO from BASF AG), ethyl 2,4,6-trimethylbenzoylphenyl phosphinate (Lucirin® TPO L from BASF AG), bis(2,4,6-trimethylbenzoyl)phenylphosphine oxide (Irgacure® 819 from Ciba Spezialitätenchemie), benzophenones, hydroxyacetophenones, phenylglyoxylic acid and derivatives thereof, or mixtures of these photoinitiators. Examples which may be mentioned are benzophenone, acetophenone, acetonaphthoquinone, methyl ethyl ketone, valerophenone, hexanophenone, α-phenylbutyrophenone, p-morpholinopropiophenone, dibenzosuberone, 4-morpholinobehzophenone, 4-morpholinodeoxybenzoin, p-diacetylbenzene, 4-aminobenzophenone, 4'-methoxyacetophenone, β-methylanthraquinone, tert-butylanthraquinone, anthraquinonecarboxylic acid esters, benzaldehyde, α-tetralone, 9-acetylphenanthrene, 2-acetylphenanthrene, 10-thioxanthenone, 3-acetylphenanthrene, 3-acetylindole, 9-fluorenone, 1-indanone, 1,3,4-triacetylbenzene, thioxanthen-9-one, xanthen-9-one, 2,4-dimethylthioxanthone, 2,4-diethylthioxanthone, 2,4-di-iso-propylthioxanthone, 2,4-dichlorothioxanthone, benzoin, benzoin iso-butyl ether, chloroxanthenone, benzoin tetrahydropyranyl ether, benzoin methyl ether, benzoin ethyl ether, benzoin butyl ether, benzoin iso-propyl ether, 7H-benzoin methyl ether, benz[de]anthracen-7-one, 1-naphthaldehyde, 4,4'-bis(dimethylamino) benzophenone, 4-phenylbenzophenone, 4-chlorobenzophenone, Michler's ketone, 1-acetonaphthone, 2-acetonaphthone, 1-benzoylcyclohexan-1-ol, 2-hydroxy-2,2-dimethylacetophenone, 2,2-dimethoxy-2-phenylacetophenone, 2,2-diethoxy-2-phenylacetophenone, 1,1-dichloroacetophenone, 1-hydroxyacetophenone, acetophenone dimethyl ketal, o-methoxybenzophenone, triphenylphosphine, tri-o-tolylphosphine, benz[a]anthracene-7,12-dione, 2,2-diethoxyacetophenone, benzil ketals, such as benzil dimethyl ketal, 2-methyl-1-[4-(methylthio)phenyl]-2-morpholinopropan-1-one, anthraquinones, such as 2-methylanthraquinone, 2-ethylanthraquinone, 2-tert-butylanthraquinone, 1-chloroanthraquinone, 2-amylanthraquinone and 2,3-butanedione.

Also suitable are photoinitiators of the phenylglyoxalic acid ester type which have little or no tendency toward yellowing, as described in DE-A 198 26 712, DE-A 199 13 353 or WO 98/33761.

The acyl- and bisacylphosphine derivatives of the formula (I) according to the invention or the compounds prepared by the process according to the invention are particularly suitable as starting compounds for the preparation of novel photoinitiators, for example those described in the German patent applications with the title "Alkoxylated Mono- and Bisacylphosphine Derivatives" and the file reference 102 06 097.5 and the title "Mono- and Bisacylphosphine Derivatives" and the file reference 102 06 096.7 with the application date Feb. 13, 2002.

Preference is given to the reaction of the acyl- and bisacylphosphine derivatives of the formula (I) according to the invention with compounds which themselves carry a (co) polymerizable group and additionally a group which is capable of reaction with the substances of the formula (I) according to the invention.

Through the leaving group FG, the compounds (I) according to the invention can be chemically coupled to compounds which contain, for example, free hydroxyl, amino, monoalkylamino, monoarylamino and/or mercapto groups. These can preferably be compounds which are themselves polymerizable compounds, i.e. carry at least one (co)polymerizable group, or compounds which carry a group which acts as photoinitiator, for example acylphosphine oxides, bisacylphosphine oxides, benzophenones, acetophenones or phenylglyoxylic acid esters, or those which carry reactive groups which are themselves able to interact with a polymer.

Particular preference is given to the reaction with compounds which carry at least one (co)polymerizable group.

(Co)polymerizable groups can be those which have unsaturated bonds, preferably carbon-carbon double bonds.

These can be, for example, free-radical- or cationically polymerizable groups.

Free-radical-(co)polymerizable groups are, for example, isolated ethylenically unsaturated groups, conjugated unsaturated groups, vinyl-aromatic groups, vinylic and vinylidene chloridic groups, N-vinylamides, vinylpyrrolidones, vinyl lactams, vinyl esters, (meth)acrylic esters or acrylonitriles.

Cationically (co)polymerizable groups are, for example, isobutylene units or vinyl ethers.

Compounds of this type which can be reacted with the acyl- and bisacylphosphine derivatives (I) according to the invention can be, for example, monoesters of a,β-unsaturated carboxylic acids, such as acrylic acid, methacrylic acid (abbreviated to "(meth)acrylic acid" in this specification), crotonic acid, itaconic acid, fumaric acid, maleic acid, acrylamidoglycolic acid, methacrylamidoglycolic acid, or vinyl ethers with diols or polyols, which preferably contain from 2 to 20 carbon atoms and at least two hydroxyl groups, such as ethylene glycol, diethylene glycol, triethylene glycol, 1,2-propylene glycol, 1,3-propylene glycol, 1,1-dimethyl-1,2-ethanediol, dipropylene glycol, tetraethylene glycol, pentaethylene glycol, tripropylene glycol, 1,4-butanediol, 1,5-pentanediol, neopentyl glycol, 1,6-hexanediol, 2-methyl-1,5-pentanediol, 2-ethyl-1,4-butanediol, 1,4-dimethylolcyclohexane, glycerol, trimethylolethane, trimethylolpropane, trimethylolbutane, pentaerythritol, ditrimethylolpropane, erythritol, sorbitol, poly-THF having a molecular weight of from 162 to 2000, poly-1,3-propanediol having a molecular weight of from 134 to 400 or polyethylene glycol having a molecular weight of from 238 to 458. It is furthermore also possible to use esters or amides of (meth)acrylic acid with aminoalcohols, for example 2-aminoethanol, 2-(methylamino)ethanol, 3-amino-1-propanol, 1-amino-2-propanol or 2-(2-aminoethoxy)ethanol, 2-mercaptoethanol or polyaminoalkanes, such as ethylenediamine or diethylenetriamine, or vinylacetic acid.

Also suitable are unsaturated polyetherols or polyesterols or polyacrylate-polyols which have a mean OH functionality of from 2 to 10 and preferably have a molecular weight of from 200 to 2000.

Examples of amides of ethylenically unsaturated carboxylic acids with aminoalcohols are hydroxyalkyl(meth)acrylamides, such as N-hydroxymethylacrylamide, N-hydroxymethylmethacrylamide, N-hydroxyethylacrylamide, N-hydroxyethylmethacrylamide, 5-hydroxy-3-oxapentyl (meth)acrylamide, N-hydroxyalkylcrotonamides, such as N-hydroxymethylcrotonamide, or N-hydroxyalkylmaleimides, such as N-hydroxyethylmaleimide.

For the reaction with (I), preference is given to the use of 2-hydroxyethyl(meth)acrylate, 2- or 3-hydroxypropyl(meth)acrylate, 1,4-butanediol mono(meth)acrylate, neopentyl glycol mono(meth)acrylate, glycerol mono- and di(meth)acrylate, trimethylolpropane mono- and di(meth)acrylate, pentaerythritol mono-, di- and tri(meth)acrylate and 4-hydroxybutyl vinyl ether, 2-aminoethyl(meth)acrylate, 2-aminopropyl(meth)acrylate, 3-aminopropyl(meth)acrylate, 4-aminobutyl(meth)acrylate, 6-aminohexyl(meth)acrylate, 2-thioethyl(meth)acrylate, 2-aminoethyl(meth)acrylamide, 2-aminopropyl(meth)acrylamide, 3-aminopropyl(meth)acrylamide, 2-hydroxyethyl(meth)acrylamide, 2-hydroxypropyl(meth)acrylamide or 3-hydroxypropyl(meth)acrylamide. Particular preference is given to 2-hydroxyethyl acrylate, 2-hydroxyethyl methacrylate, 2- or 3-hydroxypropyl acrylate, 1,4-butanediol monoacrylate and 3-(acryloxy)-2-hydroxypropyl methacrylate.

In this way, it is possible to prepare compounds which can be incorporated into the polymer in a polymerization by means of the polymerizable groups, but which, on the other hand, also act as photoinitiators, which significantly reduces the migration capability of the photoinitiators.

The acyl- and bisacylphosphine derivatives of the formula (I) according to the invention exhibit a migration tendency which is generally lower than most conventional acylphosphine oxide compounds, even without reaction with compounds containing polymerizable groups, since they are capable of reacting, through their reactive group FG, with reactive centers in the components which form the radiation-curable compositions, enabling the compounds according to the invention to be bonded, for example, to the binder of the radiation-curable compositions with formation of a chemical bond.

For example, free hydroxyl, amino, monoalkylamino, monoarylamino and/or mercapto groups are capable of functioning as reactive centers in radiation-curable compositions.

Accordingly, the invention also relates to radiation-curable compositions which are obtainable by reaction of at least one acyl- or bisacylphosphine derivative of the formula (I) or prepared by the process according to the invention with a radiation-curable composition containing free hydroxyl, amino, monoalkylamino, monoarylamino and/or mercapto groups.

Suitable radiation-curable compositions comprise, for example, at least one polymerizable compound having one or more (co)polymerizable, ethylenically unsaturated groups and one or more reactive centers.

These can be, for example, urethane, melamine, polyesterol, polyetherol, epoxide or carbonate acrylates, methacrylates or vinyl ethers containing reactive centers.

The preparation of urethane, melamine, polyesterol, polyetherol, epoxide or carbonate acrylates, methacrylates or vinyl ethers of this type is known per se to the person skilled in the art. The number of reactive centers and ethylenically unsaturated groups can be adjusted through suitable mixing of the individual components.

The number average molecular weight $M_n$ of the polymerizable compounds which can be employed is not restricted. It can be, for example, below 20,000, preferably below 15,000, particularly preferably below 10,000 and in particular below 6000.

The polydispersity $M_w/M_n$, the quotient of the number average molecular weight and the weight average molecular weight of the polymerizable compounds, represents a measure of the molecular weight distribution of the polymerizable compounds and in the ideal case has the value 1, but in practice values below 4.0, in particular below 3.5, are also satisfactory.

The data on the polydispersity and the number average and weight average molecular weights $M_n$ and $M_w$ are based here on gel permeation chromatography measurements, with polystyrene as standard and tetrahydrofuran as eluent. The method is described in Analytiker Taschenbuch, Vol. 4, pages 433 to 442, Berlin, 1984.

The compounds of the formula (I) according to the invention react, after mixing with the radiation-curable composition, with the reactive centers thereof and are thus bound in a migration-resistant manner.

The coating compositions prepared with the incorporable photoinitiators according to the invention are particularly suitable for use in packaging systems, particularly preferably in the foods sector.

Preference is given to compositions which have from 0.005 to 0.5 mol, particularly preferably 0.01-0.3 mol, very particularly preferably 0.05-0.2 mol and in particular 0.07-0.15 mol of hydroxyl groups per 100 g of substance.

Between 0.05 and 1.0 mol, preferably from 0.1 to 0.9 mol, particularly preferably from 0.2 to 0.8 mol, very particularly preferably from 0.25 to 0.75 mol and in particular from 0.3 to 0.5 mol, of the acyl- and bisacylphosphine derivatives of the formula (I) according to the invention are usually used per mol of hydroxyl groups in the radiation-curable composition.

The bonding of the compounds of the formula (I) according to the invention to the reactive centers is generally carried out at a temperature between room temperature and the curing temperature of the radiation-curable composition obtainable in this way. Typical temperatures are 40-120° C., preferably 50-110° C. and particularly preferably 60-100° C.

In the course of the curing or bonding process, the temperature can be kept constant or increased.

The duration of the thermal treatment is generally between a few minutes and several hours, for example from 1 minute to 5 hours, preferably from 2 minutes to 3 hours, particularly preferably from 5 minutes to 2 hours and in particular from 10 minutes to 1 hour.

It has furthermore been found that compounds of the generic formula (I') known from the prior art can be used as photoinitiators which conform to the formula (I), but contain a different FG group.

FG in the formula (I') has the following meanings:

FG is —Br, —$(NR^3)$—$NR^4R^9$, —$(NR^3)$—$OR^9$ or —$SR^3$ (for Z=S), and $R^9$ is hydrogen or $C_1$- to $C_4$-alkyl, where $R^3$ and $R^4$ are as defined above.

Preferred photoinitiators are compounds in which FG=Br or —$SR^3$.

Radiation-curable compositions typically comprise
(A) at least one polymerizable compound having one or more copolymerizable, ethylenically unsaturated groups,
(B) if desired reactive thinners,
(C) at least one photoinitiator according to the invention and, if desired, at least one further photoinitiator known per se, and (D) if desired further additives which are typical in surface coatings.

Typical compositions are, for example, (A) 40-100% by weight, preferably 50-90% by weight, particularly preferably 60-90% by weight and in particular 60-80% by weight, (B) 0-60% by weight, preferably 5-50% by weight, particularly preferably 6-40% by weight and in particular 10-30% by weight, (C) 0.1-20% by weight, preferably 0.5-15% by weight, particularly preferably 1-10% by weight and in particular 2-5% by weight, and (D) 0-50% by weight, preferably 2-40% by weight, particularly preferably 3-30% by weight and in particular 5-20% by weight, with the proviso that the sum is always 100% by weight.

In specific applications, the proportion of additives (D) which are typical in surface coatings can be up to 90% by weight. In this case, the proportions of the other components are reduced correspondingly.

Compounds (A) can be, for example, the urethane, melamine, polyesterol, polyetherol, epoxide or carbonate acrylates, methacrylates or vinyl ethers mentioned above.

The compounds (A) are preferably vinyl ether or (meth)acrylate compounds, particularly preferably in each case the acrylate compounds, i.e. the derivatives of acrylic acid.

Preferred vinyl ether and (meth)acrylate compounds (A) contain from 2 to 20, preferably from 2 to 10 and very particularly preferably from 2 to 6 copolymerizable, ethylenically unsaturated double bonds.

Particular preference is given to compounds (A) having a content of ethylenically unsaturated double bonds of 0.1-0.7 mol/100 g, very particularly preferably 0.2-0.6 mol/100 g.

Suitable reactive thinners (compounds (B)) are free-radical-polymerizable compounds, preferably radiation-curable compounds containing an ethylenically unsaturated, copolymerizable group, or mixtures thereof.

Mention may be made, for example, of $\alpha,\beta$-unsaturated carboxylic acids, $C_1$-$C_{20}$-alkyl(meth)acrylates, vinylaromatic compounds having up to 20 carbon atoms, vinyl esters of carboxylic acids containing up to 20 carbon atoms, ethylenically unsaturated nitriles, vinyl ethers of alcohols containing from 1 to 10 carbon atoms, and aliphatic hydrocarbons having from 2 to 8 carbon atoms and one or two double bonds.

For the purposes of this specification, the term (meth)acrylic acid is used for acrylic acid and methacrylic acid.

$\alpha,\beta$-Unsaturated carboxylic acids which can be used are, for example, acrylic acid, methacrylic acid, maleic acid or monoesters thereof, 3-acryloxypropionic acid, maleic anhydride, fumaric acid or monoesters thereof, or crotonic acid.

Preferred alkyl(meth)acrylates are those containing a $C_1$-$C_{10}$-alkyl radical, such as methyl methacrylate, methyl acrylate and ethyl acrylate.

Mixtures of the alkyl(meth)acrylates are also particularly suitable.

Vinyl esters of carboxylic acids having from 1 to 20 carbon atoms are, for example, vinyl laurate, vinyl stearate, vinyl propionate and vinyl acetate.

Suitable vinylaromatic compounds are, for example, vinyltoluene, $\alpha$-butylstyrene, 4-n-butylstyrene, 4-n-decylstyrene and preferably styrene.

Examples of nitriles are acrylonitrile and methacrylonitrile.

Examples of suitable vinyl ethers are vinyl methyl ether, vinyl isobutyl ether, vinyl hexyl ether and vinyl octyl ether.

Non-aromatic hydrocarbons having from 2 to 8 carbon atoms and one or two olefinic double bonds which may be mentioned are butadiene, isoprene, as well as ethylene, propylene and isobutylene.

It is also possible to employ N-vinylformamide, N-vinylpyrrolidone and N-vinylcaprolactam.

The additives (D) which are typical in surface coatings can be, for example, antioxidants, oxidation inhibitors, stabilizers, activators (accelerators), fillers, pigments, dyes, degassing agents, luster agents, antistatic agents, flame inhibitors, thickeners, thixotropic agents, flow-control agents, binders, antifoaming agents, fragrances, surface-active agents, viscosity modifiers, plasticizers, tackifying resins (tackifiers), chelating agents or compatibilizers.

The coating of substrates with the radiation-curable compositions is carried out by conventional methods known to the person skilled in the art, in which at least one radiation-curable composition according to the invention, for example in the form of a dispersion or alternatively without a solvent, is applied in the desired thickness to the substrate to be coated, and the volatile constituents of the dispersion are removed, if necessary with heating. This operation can, if desired, be repeated one or more times.

The application to the substrate can be carried out in a known manner, for example by spraying, dipping, knife coating, using an air blade, brushing, rolling or curtain coating. The coating thickness is generally in the range from about 3 to 1000 g/m$^2$ and preferably from 10 to 200 g/m$^2$.

Also disclosed is a process for the coating of substrates in which a coating composition comprising a substance according to the invention, if desired as a surface-coating formulation to which further additives which are typical in surface coatings and/or thermally curable resins have been added, is applied to the substrate, if desired dried, thermally treated at the curing temperature indicated above, and subsequently cured, if desired at temperatures up to the level of the curing temperature, with active radiation under an oxygen-containing atmosphere, for example air, or preferably under an inert gas.

The process for the coating of substrates can also be carried out by, after application of the mixture or surface-coating formulation according to the invention, firstly effecting curing with active radiation under an oxygen-containing atmosphere, for example air, or preferably under an inert gas, and subsequently carrying out a thermal treatment at the curing temperature.

Thermal and radiation curing can of course also be carried out in parallel.

The curing of the films formed on the substrate can, if desired, be carried out exclusively thermally. In general, however, the coatings are cured both by irradiation with high-energy radiation and also thermally.

If desired, if a plurality of layers of the coating composition are applied one on top of the other, thermal and/or radiation curing can be carried out after each coating operation.

Examples of active energy rays are ultraviolet rays, X-rays and electron beams, preferably ultraviolet rays and electron beams.

The coating of substrates can also be carried out as follows:
i) a substrate is coated with a mixture according to the invention, as described above,
ii) volatile constituents of the mixture according to the invention are removed for film formation under conditions under which the initiator (C) essentially still forms no free radicals,
iii) if desired, the film formed in step ii) is irradiated with high-energy radiation, during which the film is pre-cured, and the article coated with the pre-cured film is, if desired, subsequently treated mechanically or the surface of the pre-cured film is brought into contact with another substrate, iv) the film is thermally cured to completion.

Steps iv) and iii) can also be carried out in the reverse sequence, i.e. the film can firstly be cured thermally and then with high-energy radiation.

Typical curing temperatures are 40-120° C., preferably 50-110° C. and particularly preferably 60-100° C.

In the course of the curing process, the temperature can be kept constant or increased.

The curing duration is generally between a few minutes and several hours, for example from 1 minute to 5 hours, preferably from 2 minutes to 3 hours, particularly preferably from 5 minutes to 2 hours and in particular from 10 minutes to 1 hour.

Suitable radiation sources for the radiation curing are, for example, mercury low-pressure emitters, medium-pressure emitters or high-pressure emitters and fluorescent tubes, pulsed emitters, metal-halide emitters, xenon lamps, electrode-less discharge lamps, carbon arc lamps, electronic flash devices, which enable radiation curing without a photoinitiator, or excimer emitters. The radiation curing is carried out through exposure to high-energy radiation, i.e. UV radiation or daylight, preferably light having a wavelength in the range from $\lambda$=150 to 700 nm, particularly preferably from $\lambda$=200 to 500 nm and very particularly preferably from $\lambda$=250 to 400 nm, or by irradiation with high-energy electrons (electron beam; from 50 to 1000 keV, preferably from 100 to 500 keV and particularly preferably from 150 to 300 keV) using devices of, for example, the Cockroft-Walton type, van de Graaff type or resonance type. The radiation sources used are, for example, high-pressure mercury vapor lamps, lasers, pulsed lamps (flashlight), halogen lamps or excimer emitters. The radiation dose which is usually sufficient for crosslinking in the case of UV curing is in the range from 80 to 3000 mJ/cm$^2$.

It is of course also possible to employ a plurality of radiation sources for the curing, for example from two to four.

These can also emit in different wavelength ranges.

Since the chromophore of the acylphosphine oxide has an absorption band in the visible wavelength range above 400 nm, the photoinitiators according to the invention can also be employed with a radiation source having a low or even no UV content.

Daylight curing is likewise possible, albeit generally slower than curing with active energy radiation.

Thus, for example, the absorption spectrum of the compound I-1 essentially corresponds to that of Lucirin TPO, it being crucial that the absorption range extends into the region of visible light.

The irradiation can, if desired, also be carried out with exclusion of oxygen, for example under an inert-gas atmosphere. Suitable inert gases are preferably nitrogen, noble gases, carbon dioxide, or combustion gases. The irradiation can furthermore be carried out by masking the coating composition with transparent media. Transparent media are, for example, plastic films, glass or liquids, for example water. Irradiation is particularly preferably carried out in the manner as described in DE-A 199 57 900.

The following examples are intended to explain the invention, but without representing a restriction thereto.

EXAMPLES

"Parts" here are taken to mean "parts by weight", unless specified otherwise.

Example 1

Trimethylbenzoylphenylphosphinic acid sodium salt 644 g of ethyl trimethylbenzoylphenylphosphinate (Lucirin® TPO-L, BASF AG) were initially introduced in 3000 ml of ethyl methyl ketone, and 1.1 equivalents (285 g) of sodium iodide were added to the solution. After 15 minutes, the homogeneous solution was heated to 65° C. and stirred for 24 hours. The yellow precipitate was filtered off with suction and washed with 2×500 ml of petroleum ether. The filter cake was dried at 60° C. under reduced pressure. 530 g (85% of theory) of pale-yellow powder were isolated.

$^{31}$P-NMR (d$_6$-DMSO): δ (ppm)=10.8 $^1$H-NMR (d$_6$-DMSO): δ (ppm)=2.2 (s, 6H), 2.25 (s, 3H), 6.6 (s, 2H), 7.3 (m, 3H), 7.6 (m, 2H)

Example 2

Trimethylbenzoylphenylphosphinic acid 401.55 g of the sodium salt from Example 1 were dissolved in 1500 ml of water acidified to pH 1 with 1300 ml of 0.5 molar sulfuric acid. After 1 hour, the crystal batch which had precipitated was filtered off with suction, washed twice with 700 ml of water each time and sucked dry. The filter cake was dried azeotropically with 1500 ml of toluene in a water separator. The clear, pale-yellow toluene solution was evaporated at 50° C., and the acid was recrystallized from 2150 ml of ethyl acetate. The crystals were filtered off with suction at 0°, washed with ethyl acetate and dried at 60° C. under reduced pressure. Weight: 300 g (80% of theory) of pale-yellow crystals.

$^{31}$P-NMR (d$_6$-DMSO): δ (ppm)=17.4 1H-NMR (d$_6$-DMSO): δ (ppm)=2.1 (s, 6H), 2.3 (s, 3H), 6.7 (s, 2H), 7.35 (m, 2H), 7.6 (m, 1H), 7.75 (m, 2H)

Example 3

Trimethylbenzoylphenylphosphinyl chloride 250 g of the acid from Example 2 were suspended in 670 ml of toluene and dissolved with 102.6 g of pyridine. 1546 g of thionyl chloride were added dropwise to the reaction mixture at 60° C. over the course of 1 hour. After a post-reaction time of 3 hours, the red-brown emulsion was cooled to 0° C., and the rust-brown crystals were filtered off. The solution which remained was evaporated under reduced pressure.

Product weight: 265 g (91% of theory). $^{31}$P-NMR (d$_6$-DMSO): δ (ppm)=28.4 $^1$H-NMR (d$_6$-DMSO): δ (ppm)=1.7 (s, 6H), 1.8 (s, 3H), 6.4 (s, 2H; mesityl-CH), 7.15 (m, 2H), 7.25 (m, 1H), 7.55 (m, 2H)

Example 4

Reaction with hydroxyethyl acrylate

A solution of 100 ml of toluene, 7.34 g of triethylamine and 19.07 g of the chloride from Example 3 was warmed to 50° C. under a nitrogen atmosphere. 6.01 g of hydroxyethyl acrylate were metered in portions over the course of 30 minutes. The temperature rose to 60° C. After a further two hours at 50° C., the reaction mixture was cooled to room temperature, and 20 ml of deionized water were added. The organic phase was extracted three times with 30 ml of saturated sodium chloride solution each time. The organic phase dried over sodium sulfate was evaporated to dryness, giving 18.52 g of the product as a brownish oil.

Purity 98% (according to HPLC, retention time 7 minutes, HPLC analysis: Kontron Instruments HPLC-Pump 422, Lichrosorb 18 7, Bischoff Chromatography, Shimadzu C-R6A Chromatopac, Mitlon Roy Spectro Monitor 3100 (230 nm), acetonitrile/water/phosphoric acid (ratio 570:430:1) at 1.1 ml/min.); yield 91% of theory, purity according to $^{31}$P-NMR 100%.

Example 5

Preparation of trimethylbenzoylphenylphosphinic acid 17 g of LiCl were dissolved in 250 ml of dimethylformamide in a 2 l stirred flask fitted with internal thermometer and condenser. A solution of 86 g of ethyl trimethylbenzoylphenylphosphinate in 50 ml of DMF was subsequently added dropwise over the course of one hour. The reaction mixture was subsequently stirred overnight at 65° C. 850 ml of ice-water were added dropwise to the mixture, giving a slightly cloudy solution. After warming to 35° C., 450 ml of 0.5 M $H_2SO_4$ were added until a pH of 1.5-2 had been reached, whereupon colorless crystals were precipitated. Stirring was continued at 5° C. for one hour. The crystals were filtered off and washed twice with 200 ml of water each time. Drying gave 71.7 g of 98% pure trimethylbenzoylphenylphosphinic acid (HPLC).

Example 6

Preparation of trimethylbenzoylphenylphosphinic acid 10 g of ethyl trimethylbenzoylphenylphosphinate and 3.75 g of 1-methylimidazole hydrochloride were combined under a nitrogen atmosphere in a 250 ml four-necked flask with Teflon blade stirrer and condenser, and the mixture was stirred at 110° C. for 5.5 hours. The heating source was subsequently removed, 100 ml of ice-water were added dropwise with vigorous stirring, and the mixture was stirred for a further 10 minutes. An organic/aqueous emulsion formed, which was acidified to pH=1 using 35 ml of 0.5 molar sulfuric acid at about 50° C. with vigorous stirring, cooled to 0° C. and stirred for a further 1 hour. The precipitate which formed was filtered off with suction, washed twice with 25 ml of water each time and dried.

The crude product was recrystallized from 40 ml of ethyl acetate and dried. 7.42 g of trimethylbenzoylphenylphosphinic acid were isolated. The content according to HPLC was >98%.

The invention claimed is:

1. An acyl- or bisacylphosphine derivative of the formula (I)

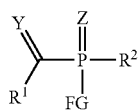

(I)

where

R$^1$ is α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4-or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or an ortho-substituted phenyl other than 2-methylphenyl, 2-methoxyphenyl or 2-chlorophenyl, R$^2$, R$^5$, R$^6$ and R$^7$ are C$_1$-C$_{18}$-alkyl, or C$_2$-C$_{18}$-alkyl, C$_2$-C$_{18}$-alkenyl, C$_6$-C$_{12}$-aryl or C$_5$-C$_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals, R$^2$ is furthermore C$_1$-C$_{18}$-alkoxy, which is unsubstituted or substituted by aryl, alkyl, aryloxy, alkoxy, heteroatoms and/or heterocyclic radicals, or is R$^1$—(C═Y)—, Y is O, S, NR$^3$, N—OR$^3$ or N—NR$^3$R$^4$, Z is O, S, NR$^3$, N—OR$^3$, N—NR$^3$R$^4$ or a free pair of electrons, R$^3$ is hydrogen, C$_1$- to C$_4$-alkyl, SO$_3$H, phenyl or acetyl, R$^4$ is hydrogen, C$_1$- to C$_4$-alkyl, COOR$^3$, or C$_6$-C$_{12}$-aryl or arylsulfonyl, each of which is unsubstituted or substituted by aryl, alkyl, aryloxy, alkoxy, heteroatoms and/or heterocyclic radicals, FG is a leaving group having the structure —Cl, —CN, —OCN, —SCN, —N$^+$R$^6$R$^7$R$^8$, —O(CO)R$^5$, —O(CO)OR$^5$, —O(SO)Cl, —O(SO$_2$)OR$^5$, —O(SO$_2$)R$^5$ or —O(CO)Cl, R$^5$ is furthermore C$_1$-C$_{18}$-alkoxy, which is unsubstituted or substituted by aryl, alkyl, aryloxy, alkoxy, heteroatoms and/or heterocyclic radicals, and R$^8$ is C$_1$-C$_{18}$-alkyl, which is unsubstituted or substituted by aryl, alkyl, aryloxy, alkoxy, heteroatoms and/or heterocyclic radicals, or C$_2$-C$_{18}$-alkyl, which is uninterrupted or interrupted by one or more oxygen and/or sulfur atoms and/or one or more substituted or unsubstituted imino groups.

2. An acyl- or bisacylphosphine derivative as claimed in claim 1, where

Y is O, S or NR$^3$,

Z is O, S, NR$^3$ or a free pair of electrons,

FG is —Cl, —O(CO)R$^5$, —O(CO)OR$^5$, —O(SO)Cl, —O(SO$_2$)R$^5$ or —O(CO)Cl.

3. An acyl- or bisacylphosphine derivative as claimed in claim 1, where

Y is O or S,

Z is O, S or a free pair of electrons,

FG is —Cl, —O(CO)R$^5$, —O(CO)OR$^5$ or —O(SO$_2$)R$^5$.

4. An acyl- or bisacylphosphine derivative as claimed in claim 1, where
Y is O,
Z is O or a free pair of electrons,
FG is —Cl or —O(SO$_2$)R$^5$.

5. An acyl- or bisacylphosphine derivative as claimed in claim 1, where
R$^1$ is 2,4,6-trimethylphenyl, 2,6-dimethylphenyl, 2,6-dimethoxyphenyl, 2,6-dichlorophenyl, or 2,4,6-trichlorophenyl, and
R$^2$ is phenyl or ethoxy.

6. A process for the preparation of an acyl- or bisacylphosphine derivative of the formula (I)

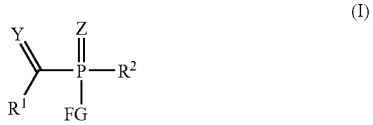
(I)

where
R$^1$, R$^2$, R$^5$, R$^6$ and R$^7$ are C$_1$-C$_{18}$-alkyl, or C$_2$-C$_{18}$-alkyl, C$_2$-C$_{18}$-alkenyl, C$_6$-C$_{12}$-aryl or C$_5$-C$_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals,
R$^2$ is furthermore C$_1$-C$_{18}$-alkoxy, which is unsubstituted or substituted by aryl, alkyl, aryloxy, alkoxy, heteroatoms and/or heterocyclic radicals, or is R$^1$—(C=Y)—,
Y is O, S, NR$^3$, N—OR$^3$ or N—NR$^3$R$^4$,
Z is O, S, NR$^3$, N—OR$^3$, N—NR$^3$R$^4$ or a free pair of electrons,
R$^3$ is hydrogen, C$_1$- to C$_4$-alkyl, SO$_3$H, phenyl or acetyl,
R$^4$ is hydrogen, C$_1$- to C$_4$-alkyl, COOR$^3$, or C$_6$-C$_{12}$-aryl or arylsulfonyl, each of which is unsubstituted or substituted by aryl, alkyl, aryloxy, alkoxy, heteroatoms and/or heterocyclic radicals,
FG is a leaving group having the structure —F, —Cl, —I, —CN, —OCN, —SCN, —N$^+$R$^6$R$^7$R$^8$, —O(CO)R$^5$, —O(CO)OR$^5$, —O(SO)Cl, —O(SO$_2$)Cl, —O(SO$_2$)R$^5$, —O(CO)Cl, —O(NO)OR$^5$ or, in the case where Z≠S, —SR$^5$,
R$^5$ is furthermore C$_1$-C$_{18}$-alkoxy, which is unsubstituted or substituted by aryl, alkyl, aryloxy, alkoxy, heteroatoms and/or heterocyclic radicals, and
R$^8$ is C$_1$-C$_{18}$-alkyl, which is unsubstituted or substituted by aryl, alkyl, aryloxy, alkoxy, heteroatoms and/or heterocyclic radicals, or C$_2$-C$_{18}$-alkyl, which is uninterrupted or interrupted by one or more oxygen and/or sulfur atoms and/or one or more substituted or unsubstituted imino groups,
from a substance of the formula (II)

(II)

where
X is hydrogen or a cation,
which comprises reacting substance (II) with at least one agent which converts the —OX group into an —FG group.

7. A process as claimed in claim 6, wherein substance (II) is reacted with phosgene (COCl$_2$), thionyl chloride (SOCl$_2$) or sulfuryl chloride (SO$_2$Cl$_2$) in order to convert —OX into the group FG=—Cl.

8. A process as claimed in claim 6, wherein substance (II) is reacted with R$^5$SO$_2$Cl or (R$^5$SO$_2$)$_2$O in order to convert —OX into the group FG=—OSO$_2$R$^5$.

9. A method of photoinitiation comprising photoinitiating a potopolymerizable compositions with an acyl- or bisacylphosphine derivative of the formula (I)

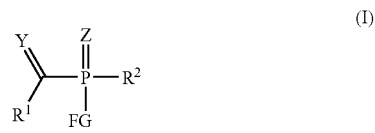
(I)

where
R$^1$ is phenyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or an ortho-substituted phenyl other than 2-methylphenyl, 2-methoxyphenyl or 2-chlorophenyl,
R$^2$, R$^5$ and R$^7$ are C$_1$-C$_{18}$-alkyl, or C$_2$-C$_{18}$-alkyl, C$_2$-C$_{18}$-alkenyl, C$_6$-C$_{12}$-aryl or C$_5$-C$_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals,
R$^2$ is furthermore C$_1$-C$_{18}$-alkoxy is unsubstituted or substituted by aryl, alkyl, aryloxy, alkoxy, heteroatoms and/or heterocylic radicals, or is R$^1$—(C=Y)—,
Y is O, S, NR$^3$, N—OR$^3$ or N—NR$^3$R$^4$,
Z is O, S, NR$^3$, N—OR$^3$, N—NR$^3$R$^4$ or a free pair of electrons,
R$^3$ is hydrogen, C$_1$- to C$_4$-alkyl, SO$_3$H, phenyl or acetyl,
R$^4$ is hydrogen, C$_1$- to C$_4$-alkyl, COOR$^3$, or C$_6$-C$_{12}$-aryl or arylsulfonyl, each of which is unsubstituted or substituted by aryl, alkyl, aryloxy, alkoxy, heteroatoms and/or heterocyclic radicals,
FG is a leaving group having the structure —Cl, —CN, —OCN, —SCN, —N$^+$R$^6$R$^7$R$^8$, —O(CO)R$^5$, —O(CO)OR$^5$, —O(SO)Cl, —O(SO$_2$)OR$^5$, —O(SO$_2$)R$^5$ or —O(CO)Cl, $R^5$ is furthermore $C_1$-$C_{18}$-alkoxy, which is unsubstituted or substituted by aryl, alkyl, aryloxy, alkoxy, heteroatoms and/or heterocyclic radicals, and $R^8$ is $C_1$-$C_{18}$-alkyl, which is unsubstituted or substituted by aryl, alkyl, aryloxy, alkoxy, heteroatoms and/or heterocyclic radicals, or $C_2$-$C_{18}$-alkyl, which is uninterrupted or interrupted by one or more oxygen and/or sulfur atoms and/or one or more substituted or unsubstituted imino groups.

10. A method of photoinitiation comprising photoinitiating a potopolymerizable compositions with an acyl- or bisacylphosphine derivative of the formula (I)

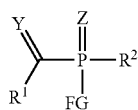
(I)

where $R^1$ is phenyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or an ortho-substituted phenyl other than 2-methylphenyl, 2-methoxyphenyl or 2-chlorophenyl, $R^2$, $R^5$, $R^6$ and $R^7$ are $C_1$-$C_{18}$-alkyl, or $C_2$-$C_{18}$-alkyl, $C_2$-$C_{18}$-alkenyl, $C_6$-$C_{12}$-aryl or $C_5$-$C_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals, $R^2$ is furthermore which is unsubstituted substituted by aryl, alkyl, aryloxy, alkoxy, heteroatoms and/or heterocyclic radicals, or is $R^1$—(C=Y)—, Y is O, S, $NR^3$, N—$OR^3$ or N—$NR^3R^4$, Z is O, S, $NR^3$, N—$OR^3$, N—$NR^3R^4$ or a free pair of electrons, $R^3$ is hydrogen, $C_1$- to $C_4$-alkyl, $SO_3H$, phenyl or acetyl, $R^4$ is hydrogen, $C_1$- to $C_4$-alkyl, $COOR^3$, or $C_6$-$C_{12}$-aryl or arylsulfonyl, each of which is unsubstituted or substituted by aryl, alkyl, aryloxy, alkoxy, heteroatoms and/or heterocyclic radicals, $R^5$ is furthermore $C_1$-$C_{18}$-alkoxy, which is unsubstituted or substituted by aryl, alkyl, aryloxy, alkoxy, heteroatoms and/or heterocyclic radicals, $R^8$ is $C_1$-$C_{18}$-alkyl, which is unsubstituted or substituted by aryl, alkyl, aryloxy, alkoxy, heteroatoms and/or heterocyclic radicals, or $C_2$-$C_{18}$-alkyl, which is uninterrupted or interrupted by one or more oxygen and/or sulfur atoms and/or one or more substituted or unsubstituted imino groups, and FG is defined as follows:
FG —Br, —($NR^3$)—$NR^4R^9$, —($NR^3$)—$OR^9$ or —$SR^3$ (for Z=S), and $R^9$ is hydrogen or $C_1$- to $C_4$-alkyl.

11. A photoinitiator mixture comprising at least one acyl- or bisacyiphosphine derivative of the formula (I)

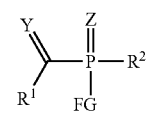
(I)

where $R^1$ is phenyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or an ortho-substituted phenyl other than 2-methylphenyl, 2-methoxyphenyl or 2-chlorophenyl, $R^2$, $R^5$, $R^6$ and $R^7$ are $C_1$-$C_{18}$-alkyl, or $C_2$-$C_{18}$-alkyl, $C_2$-$C_{18}$-alkenyl, $C_6$-$C_{12}$-aryl or $C_5$-$C_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals, $R^2$ is furthermore which is unsubstituted substituted by aryl, alkyl, aryloxy, alkoxy, heteroatoms and/or heterocyclic radicals, or is $R^1$—(C=Y)—, Y is O, S, $NR^3$, N—$OR^3$ or N—$NR^3R^4$, Z is O, S, $NR^3$, N—$OR^3$, N—$NR^3R^4$ or a free pair of electrons, $R^3$ is hydrogen, $C_1$- to $C_4$-alkyl, $SO_3H$, phenyl or acetyl, $R^4$ is hydrogen, $C_1$- to $C_4$-alkyl, $COOR^3$, or $C_6$-$C_{12}$-aryl or arylsulfonyl, each of which is unsubstituted or substituted by aryl, alkyl, aryloxy, alkoxy, heteroatoms and/or heterocyclic radicals, FG is a leaving group having the structure —Cl, —CN, —OCN, —SCN, —$N^+R^6R^7R^8$, —O(CO)$R^5$, —O(CO)$OR^5$, —O(SO)Cl, —O($SO_2$)$OR^5$, —O($SO_2$)$R^5$ or —O(CO)Cl, $R^5$ is furthermore $C_1$-$C_{18}$-alkoxy, which is unsubstituted or substituted by aryl, alkyl, aryloxy, alkoxy, heteroatoms and/or heterocyclic radicals, and $R^8$ is $C_1$-$C_{18}$-alkyl, which is unsubstituted or substituted by aryl, alkyl, aryloxy, alkoxy, heteroatoms and/or heterocyclic radicals, or $C_2$-$C_{18}$-alkyl, which is uninterrupted or interrupted by one or more oxygen and/or sulfur atoms and/or one or more substituted or unsubstituted imino groups.

12. A radiation-curable composition comprising at least one acyl- or bisacylphosphine derivative of the formula (I)

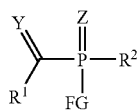
(I)

where
- $R^1$ is phenyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or an ortho-substituted phenyl other than 2-methylphenyl, 2-methoxyphenyl or 2-chlorophenyl,
- $R^2$, $R^5$, $R^6$ and $R^7$ are $C_1$-$C_{18}$-alkyl, or $C_2$-$C_{18}$-alkyl, $C_2$-$C_{18}$-alkenyl, $C_6$-$C_{12}$-aryl or $C_5$-$C_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals,
- $R^2$ is furthermore which is unsubstituted substituted by aryl, alkyl, aryloxy, alkoxy, heteroatoms and/or heterocyclic radicals, or is $R^1$—(C═Y)—,
- Y is O, S, $NR^3$, N—$OR^3$ or N—$NR^3R^4$,
- Z is O, S, $NR^3$, N—$OR^3$, N—$NR^3R^4$ or a free pair of electrons,
- $R^3$ is hydrogen, $C_1$- to $C_4$-alkyl, $SO_3H$, phenyl or acetyl,
- $R^4$ is hydrogen, $C_1$- to $C_4$-alkyl, $COOR^3$, or $C_6$-$C_{12}$-aryl or arylsulfonyl, each of which is unsubstituted or substituted by aryl, alkyl, aryloxy, alkoxy, heteroatoms and/or heterocyclic radicals,
- FG is a leaving group having the structure —Cl, —CN, —OCN, —SCN, —$N^+R^6R^7R^8$, —O(CO)$R^5$, —O(CO)O$R^5$, —O(SO)Cl, —O(SO$_2$)O$R^5$, —O(SO$_2$)$R^5$ or —O(CO)Cl,
- $R^5$ is furthermore $C_1$-$C_{18}$-alkoxy, which is unsubstituted or substituted by aryl, alkyl, aryloxy, alkoxy, heteroatoms and/or heterocyclic radicals, and
- $R^8$ is $C_1$-$C_{18}$-alkyl, which is unsubstituted or substituted by aryl, alkyl, aryloxy, alkoxy, heteroatoms and/or heterocyclic radicals, or $C_2$-$C_{18}$-alkyl, which is uninterrupted or interrupted by one or more oxygen and/or sulfur atoms and/or one or more substituted or unsubstituted imino groups.

13. A radiation-curable composition obtainable by reaction of at least one acyl- or bisacylphosphine derivative of the formula (I)

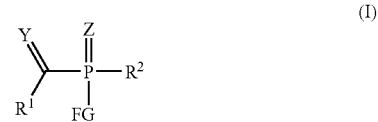
(I)

where
- $R^1$ is phenyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or an ortho-substituted phenyl other than 2-methylphenyl, 2-methoxyphenyl or 2-chlorophenyl,
- $R^2$, $R^5$, $R^6$ and $R^7$ are $C_1$-$C_{18}$-alkyl, or $C_2$-$C_{18}$-alkyl, $C_2$-$C_{18}$-alkenyl, $C_6$-$C_{12}$-aryl or $C_5$-$C_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals,
- $R^2$ is furthermore which is unsubstituted substituted by aryl, alkyl, aryloxy, alkoxy, heteroatoms and/or heterocyclic radicals, or is $R^1$—(C═Y)—,
- Y is O, S, $NR^3$, N—$OR^3$ or N—$NR^3R^4$,
- Z is O, S, $NR^3$, N—$OR^3$, N—$NR^3R^4$ or a free pair of electrons,
- $R^3$ is hydrogen, $C_1$- to $C_4$-alkyl, $SO_3H$, phenyl or acetyl,
- $R^4$ is hydrogen, $C_1$- to $C_4$-alkyl, $COOR^3$, or $C_6$-$C_{12}$-aryl or arylsulfonyl, each of which is unsubstituted or substituted by aryl, alkyl, aryloxy, alkoxy, heteroatoms and/or heterocyclic radicals,
- FG is a leaving group having the structure —Cl, —CN, —OCN, —SCN, —$N^+R^6R^7R^8$, —O(CO)$R^5$, —O(CO)O$R^5$, —O(SO)Cl, —O(SO$_2$)O$R^5$, —O(SO$_2$)$R^5$ or —O(CO)Cl,
- $R^5$ is furthermore $C_1$-$C_{18}$-alkoxy, which is unsubstituted or substituted by aryl, alkyl, aryloxy, alkoxy, heteroatoms and/or heterocyclic radicals, and
- $R^8$ is $C_1$-$C_{18}$-alkyl, which is unsubstituted or substituted by aryl, alkyl, aryloxy, alkoxy, heteroatoms and/or heterocyclic radicals, or $C_2$-$C_{18}$-alkyl, which is uninterrupted or interrupted by one or more oxygen and/or sulfur atoms and/or one or more substituted or unsubstituted imino groups, with a compound containing free hydroxyl, amino, monoalkylamino, monoarylamino and/or mercapto groups.

14. A radiation-curable composition as claimed in claim 13, wherein the compound is a polymerizable compound having a number average molecular weight $M_n$ of less than 20,000.

15. A radiation-curable composition comprising a photoinitiator mixture as claimed in claim 11.

16. An acyl- or bisacylphosphine derivative as claimed in claim 2, where
R$^1$ is 2,4,6-trimethylphenyl, 2,6-dimethylphenyl, 2,6-dimethoxyphenyl, 2,6-dichlorophenyl or 2,4,6-trichlorophenyl, and
R$^2$ is phenyl or ethoxy.

17. An acyl- or bisacylphosphine derivative as claimed in claim 3, where
R$^1$ is 2,4,6-trimethylphenyl, 2,6-dimethylphenyl, 2,6-dimethoxyphenyl, 2,6-dichlorophenyl or 2,4,6-trichlorophenyl, and
R$^2$ is phenyl or ethoxy.

18. An acyl- or bisacylphosphine derivative as claimed in claim 4, where
R$^1$ is 2,4,6-trimethylphenyl, 2,6-dimethylphenyl, 2,6-dimethoxyphenyl, 2,6-dichlorophenyl or 2,4,6-trichlorophenyl, and
R$^2$ is phenyl or ethoxy.

19. An acyl- or bisacylphosphine derivative of the formula (I)

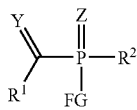

where
R$^1$ is phenyl, α-naphthyl, β-naphthyl, 2-, 3- or 4-chlorophenyl, 2,6- or 2,4-dichlorophenyl, 2,4,6-trichlorophenyl, 2-, 3- or 4-methylphenyl, 2,6- or 2,4-dimethylphenyl, 2,4,6-trimethylphenyl, 2-, 3- or 4-ethylphenyl, 2,6- or 2,4-diethylphenyl, 2-, 3- or 4-iso-propylphenyl, 2-, 3- or 4-tert-butylphenyl, 2-, 3- or 4-methoxyphenyl, 2,6- or 2,4-dimethoxyphenyl, 2,6- or 2,4-diethoxyphenyl, methylnaphthyl, 2,6-dimethylphenyl, 2,4,6-trimethylphenyl, 2,6-dimethoxyphenyl, 2,6-dichlorophenyl, 4-bromophenyl, 2- or 4-nitrophenyl, 2,4- or 2,6-dinitrophenyl, 4-dimethylaminophenyl, 4-acetylphenyl, cyclopentyl, cyclohexyl, 2,5-dimethylcyclopentyl, 2,6-dimethylcyclohexyl, 2,6-diethylcyclohexyl, 2,6-dimethoxycyclohexyl, 2,6-diethoxycyclohexyl, 2,6-dichlorocyclohexyl, 2,5-dichlorocyclopentyl, 2- or 3-furyl, 2- or 3-thiophenyl, 2- or 3-pyrryl, dimethylpyrryl or an ortho-substituted phenyl other than 2-methylphenyl, 2-methoxyphenyl or 2-chlorophenyl, R$^5$, R$^6$ and R$^7$ are C$_1$-C$_{18}$-alkyl, or C$_2$-C$_{18}$-alkyl, C$_2$-C$_{18}$-alkenyl, C$_6$-C$_{12}$-aryl or C$_5$-C$_{12}$-cycloalkyl, each of which is uninterrupted or interrupted by one or more oxygen and/or sulfur atoms and/or one or more substituted or unsubstituted imino groups, or are a five- to six-membered, oxygen, nitrogen and/or sulfur atom-containing heterocyclic radical, where the said radicals may each be substituted by aryl, alkyl, aryloxy, alkoxy, heteroatoms and/or heterocyclic radicals, Y is O, S, NR$^3$, N—OR$^3$ or N—NR$^3$R$^4$, Z is O, S, NR$^3$, N—OR$^3$, N—NR$^3$R$^4$ or a free pair of electrons, R$^3$ is hydrogen, C$_1$- to C$_4$-alkyl, SO$_3$H, phenyl or acetyl, R$^4$ is hydrogen, C$_1$- to C$_4$-alkyl, COOR$^3$, or C$_6$-C$_{12}$-aryl or arylsulfonyl, each of which is unsubstituted or substituted by aryl, alkyl, aryloxy, alkoxy, heteroatoms and/or heterocyclic radicals, FG is a leaving group having the structure —Cl, —CN, —OCN, —SCN, —N$^+$R$^6$R$^7$R$^8$, —O(CO)R$^5$, —O(CO)OR$^5$, —O(SO)Cl, —O(SO$_2$)OR$^5$, —O(SO$_2$)R$^5$ or —O(CO)Cl, R$^5$ is furthermore C$_1$-C$_{18}$-alkoxy, which is unsubstituted or substituted by aryl, alkyl, aryloxy, alkoxy, heteroatoms and/or heterocyclic radicals, R$^8$ is C$_1$-C$_{18}$-alkyl, which is unsubstituted or substituted by aryl, alkyl, aryloxy, alkoxy, heteroatoms and/or heterocyclic radicals, or C$_2$-C$_{18}$-alkyl, which is uninterrupted or interrupted by one or more oxygen and/or sulfur atoms and/or one or more substituted or unsubstituted imino groups, and R$^2$ is ethoxy.

* * * * *